US007968691B2

(12) United States Patent
England et al.

(10) Patent No.: US 7,968,691 B2
(45) Date of Patent: Jun. 28, 2011

(54) PULLULANASE VARIANTS WITH INCREASED PRODUCTIVITY

(75) Inventors: George England, Redwood City, CA (US); Marc Kolkman, Oegstgeest (NL); Brian Miller, Elgin, IL (US); Casper Vroemen, Oegstgeest (NL)

(73) Assignee: Danisco US Inc., Palo Alto, CA (US)

( * ) Notice: Subject to any disclaimer, the term of this patent is extended or adjusted under 35 U.S.C. 154(b) by 30 days.

(21) Appl. No.: 11/841,526

(22) Filed: Aug. 20, 2007

(65) Prior Publication Data

US 2008/0108126 A1  May 8, 2008

(51) Int. Cl.
*C12N 15/11* (2006.01)
*A61K 35/00* (2006.01)

(52) U.S. Cl. ............ 536/23.1; 424/94.1; 424/94.6
(58) Field of Classification Search .......... 536/23.1; 424/94.1, 94.6, 94, 6
See application file for complete search history.

(56) References Cited

U.S. PATENT DOCUMENTS

| 4,683,195 | A | 7/1987 | Mullis et al. |
| 4,760,025 | A | 7/1988 | Estell et al. |
| 5,264,366 | A | 11/1993 | Ferrari et al. |
| RE34,606 | E | 5/1994 | Estell |
| 5,605,793 | A | 2/1997 | Stemmer |
| 6,255,115 | B1 | 7/2001 | Beijersberger |
| 6,350,599 | B1 | 2/2002 | Svendsen |
| 6,429,358 | B1 | 8/2002 | Broglie .............. 800/284 |
| 6,537,776 | B1 | 3/2003 | Short |
| 6,768,001 | B2 | 7/2004 | Saloheimo et al. |
| 6,838,257 | B2 | 1/2005 | Svendsen |
| 2002/0182734 | A1 | 12/2002 | Diaz-Torres et al. |
| 2004/0121446 | A1 | 6/2004 | England et al. |

FOREIGN PATENT DOCUMENTS

| WO | 0 215 594 | 3/1987 |
| WO | WO 01/51620 A2 * | 7/2001 |
| WO | WO 02/14490 | 2/2002 |

OTHER PUBLICATIONS

Database Geneseq [Online] Feb. 9, 2006, "Bacterial pullulanase protein sequence." XP002469439 retrieved from EBI accession No. GSP : AEE27547, Database accession No. AEE27547 abstract.
Database Geneseq [Online] Sep. 24, 2001, "Bacillus deramificans pullulanase." XP002469440 retrieved from EBI accession No. GSP : AAE05690, Database accession No. AAE05690 abstract.
Database Geneseq [Online] Sep. 24, 2001, "Bacillus deramificans pullulanase DNA." XP002469441 retrieved from EBI accession No. GSN :AAD10891, Database accession No. AAD10891 abstract.

Altschul, Stephen F. et al., "Basic Local Alignment Search Tool," *J. Mol. Biol.*, 215:403-410 (1990).
Bajar, Aslam, et al., "Identification of a fungal cutinase promoter that is inducible by a plant signal via a phosphorylated trans-acting factor," *Proc. Natl. Acad. Sci. USA*, vol. 88, pp. 8208-8212, Sep. 1991.
Bennett & Lasure (1991) "More Gene Manipulations in Fungi," Academic Press, San Diego, pp. 70-76.
Boel, E. et al., "Two different types of intervening sequences in the glucoamylase gene from *Aspergillus niger*," The EMBO Journal, vol. 3, No. 7, pp. 1581-1585, 1984.
Brigidi et al., "Genetic transformation of intact cells of *Bacillus subtilis* by electroporation," (1990), *FEMS Microbiol. Lett.* 67: 135-138.
Dayhoff et al., "A Model of Evolutionary Change in Proteins," *Atlas of Protein Sequence and Structure* 5:Suppl. 3 (National Biomedical Research Foundation, Washington, D.C. (1978) pp. 345-352.
Goldman, et al., "Transformation of *Trichoderma harzianum* by high-voltage electric pulse," *Current Genetics*, 17:169-174, 1990.
Lorito, M., et al., "Biolistic transformation of *Trichoderma harzianum* and *Gliocladium virens* using plasmid and genomic DNA," *Current Genetics*, 24:349-356, 1993.
Mullaney, et al., "Primary structure of the *trpC* gene from *Aspergillus nidulans*," *Mol. Gen. Genet.*, 199:37-45, 1985.
Needleman, et al., "A General Method Applicable to the Search for Similarities in the Amino Acid Sequence of Two Proteins," (1970) *J. Mol. Biol.*, vol. 48, pp. 443-453.
Nunberg, et al., "Molecular Cloning and Characterization of the Glucoamylase Gene of *Aspergillus awamori*," *Molecular and Cellular Biology*, pp. 2306-2315, Nov. 1984.
Pearson, et al., "Improved tools for biological sequence comparison," (1988) *Proc. Natl. Acad. Sci. USA* vol. 85, pp. 2444-2448.
Penttila, et al., "A versatile transformation system for the cellulolytic filamentous fungus *Trichoderma reesei*," Gene, V61, pp. 155-164, 1987.
Shpaer, "GeneAssist—Smith Waterman and Other Database Similarity Searches and Identification of Motifs," *Methods in Molecular Biology, Sequence Data Anaylsis Guidebook*, Humana Press, Inc. 70:173-187 (1997).
Smith, et al.,"Comparison of Biosequences," *Adv. Appl. Math.* 2:482-489, 1981.
Yelton, et al., "Transformation of *Aspergillus nidulans* by using a *trpC* plasmid," *Proc. Natl. Acad. Sci.*, vol. 81, pp. 1470-1474, Mar. 1984.

* cited by examiner

*Primary Examiner* — Michael C. Wilson

(57) ABSTRACT

The invention relates to novel variants of the enzymatic peptide pullulanase, the gene sequences encoding said novel peptides, expression vectors comprising those gene sequences as well as organisms expressing the novel pullulanase variants. The novel pullulanase variants of the present invention were made empirically by the use of codon-optimization procedures, selective truncation of "wild-type" molecules and through the replacement of selected amino acid residues. Furthermore, the invention relates to the use of these novel pullulanase peptides in the textile, fermentation, food and other industries.

4 Claims, 14 Drawing Sheets

FIGURE 1
Pullulanase – current process
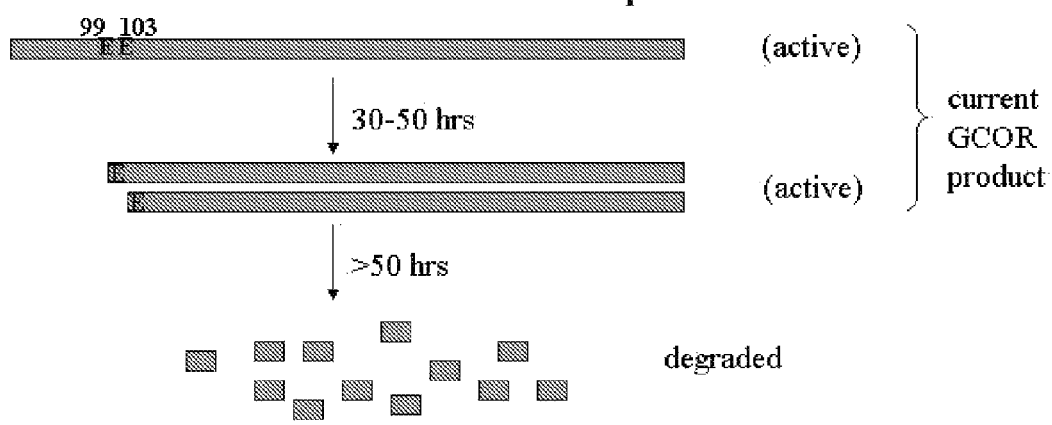
Pullulanase – new variants
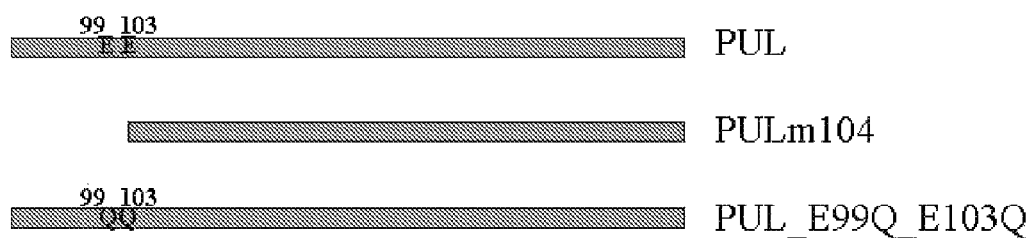

FIGURE 7A

PUL wild-type DNA nucleotide sequence
BOLD = amyL signal sequence
Black = PUL mature coding sequence

**atgaaacaacaaaaacggctttacgcccgattgctgacgctgttatttgcgctcatcttcttgc
tgcctcattctgcagcttcagca**gatggcaatacgacgacgatcatcgtccattatttagacc
ggcgggagattatcaaccgtggagcctttggatgtggccgaaagatggaggaggagcggaatat
gattttaaccagccggcagattcacttggagcagtcgcctcagcagatattccgggaaatccga
gccaagtcggcatcatcgtcagaacacaggattggacgaaagatgtcagcgccgatcgctatat
cgatctgagcaaggcaatgaagtctggctggtcgaaggcaacagccagatcttttatagcgaa
aaagacgccgaagatgctgctaaaccggcagtcagcaacgcttatctggatgccagcaaccaag
tcctggtcaaactgagccaaccgctgacacttggagaaggagcgagcggatttacggtccatga
tgacacggcgaacaaagatatcccggtcacgagcgttaaagatgctagcctgggccaagatgtc
acagcagttctggcgggcacgtttcaacatatctttggcggatcagattgggcaccggataatc
acagcacgctgctgaaaaagtcacgaacaacctgtatcagtttagcggagatctgccggaagg
caactatcaatataaagtcgccctgaacgatagctggaacaatccgagctatccgagcgataac
atcaatctgacagtcccggcaggcggagcacatgtcacgtttagctatatcccgagcacacatg
ccgtctatgacacgatcaacaacccgaacgccgatcttcaagtcgaaagcggcgtcaaaacgga
tctggtcacagtcacattgggagaagatccggatgtcagccatacactgagcatccaaacggat
ggctatcaagcgaaacaagtcatcccgagaaacgtcctgaacagcagccagtattattatagcg
gcgatgatctgggcaacacgtatacacaaaaagcgacgacgtttaaagtttgggcgccgacaag
cacacaagtcaacgtcctgctgtatgattcagcaacaggcagcgtcacaaaaatcgtcccgatg
acagcatcaggacatggagtctgggaagcgacggtcaaccaaaacctggaaaactggtattata
tgtatgaagtcacgggccaaggatcaacaagaacagcggtcgatccgtatgctacagcaatcgc
cccgaatggaacaagaggcatgatcgtcgatctggcaaaaacagacccggcaggctggaatagc
gataaacatatcacgccgaaaaacatcgaagatgaagtcatctatgaaatggacgtccgggatt
ttagcatcgatccgaacagcggcatgaaaaacaaaggcaaatatctggcgctgacggaaaaagg
aacaaaaggcccggataacgtcaaaacaggcatcgatagcctgaaacaactgggcatcacacat
gtccaactgatgccggtctttgctagcaatagcgtcgatgaaacggacccgacacaagataact
ggggctatgacccgagaaattatgatgtcccggaaggccaatatgccacgaacgccaatggaaa
cgcccggatcaaagaatttaaagaaatggtcctgagccttcatagagaacatatcggcgtcaac
atggacgtcgtctataaccatacgtttgccacacagatcagcgactttgataaaatcgtgccgg
aatattattcggacggatgacgccggcaattatacgaatggcagcggcacaggaaatgaaat
cgccgccgaaagaccgatggtccagaaatttatcatcgacagccttaaatattgggtcaacgaa
tatcatatcgacggctttcgctttgatctgatggcgctgctgggcaaagatacaatgagcaaag
cggcgagcgaacttcatgctatcaatccgggcatcgctctttatggagaaccgtggacaggagg
aacatcagcactgccggatgatcaactgctgacaaaaggcgcccaaaaaggaatgggagtcgcc
gtctttaacgacaacctgagaaatgccctggatggcaacgttttgatagcagcgcccaaggat
ttgctacaggagcgacaggactgacagatgccatcaaaaatggcgtcgaaggcagcatcaacga
ttttacaagcagcccgggagaaacgatcaattatgtcacgagccatgacaactatacgctgtgg
gacaaaatcgctctgagcaacccgaatgatagcgaagcggaccggatcaaaatggatgaactgg
cacaagcagtcgtcatgacatcacaaggcgtcccgtttatgcaaggcggagaagaaatgctgag
aacgaaaggcggcaacgacaacagctataatgccggcgatgccgtcaatgaatttgactggagc
cggaaagcacaatatccggacgtcttaactattattcaggacttatccatctgagactggacc
atccggcgtttagaatgacgacggcgaacgaaatcaacagccatcttcagtttctgaacagccc
ggaaaatacggtcgcctatgaactgacggaccatgtgaacaaagacaaatggggcaacatcatc

FIGURE 7A (continued)

```
gtcgtttataacccgaacaaaacggtcgccacaatcaatcttccgagcggcaaatgggcaatca
atgccacaagcggcaaagttggagaaagcacactgggacaagcagaaggatcagtccaagtccc
gggaatcagcatgatgatccttcatcaagaagtcagcccggaccacggcaaaaaa
```

FIGURE 7B

```
PUL wild-type protein sequence    (immature; SEQ ID NO: 2)
Bold = amyL signal sequence       (SEQ ID NO: 11)
Black = PUL mature sequence       (SEQ ID NO: 12)
```

MKQQKRLYARLLTLLFALIFLLPHSAASADGNTTTIIVHYFRPAGDYQPWSLWMWPKDGGGAEY
DFNQPADSLGAVASADIPGNPSQVGIIVRTQDWTKDVSADRYIDLSKGNEVWLVEGNSQIFYSE
KDAEDAAKPAVSNAYLDASNQVLVKLSQPLTLGEGASGFTVHDDTANKDIPVTSVKDASLGQDV
TAVLAGTFQHIFGGSDWAPDNHSTLLKKVTNNLYQFSGDLPEGNYQYKVALNDSWNNPSYPSDN
INLTVPAGGAHVTFSYIPSTHAVYDTINNPNADLQVESGVKTDLVTVTLGEDPDVSHTLSIQTD
GYQAKQVIPRNVLNSSQYYYSGDDLGNTYTQKATTFKVWAPTSTQVNVLLYDSATGSVTKIVPM
TASGHGVWEATVNQNLENWYYMYEVTGQGSTRTAVDPYATAIAPNGTRGMIVDLAKTDPAGWNS
DKHITPKNIEDEVIYEMDVRDFSIDPNSGMKNKGKYLALTEKGTKGPDNVKTGIDSLKQLGITH
VQLMPVFASNSVDETDPTQDNWGYDPRNYDVPEGQYATNANGNARIKEFKEMVLSLHREHIGVN
MDVVYNHTFATQISDFDKIVPEYYYRTDDAGNYTNGSGTGNEIAAERPMVQKFIIDSLKYWVNE
YHIDGFRFDLMALLGKDTMSKAASELHAINPGIALYGEPWTGGTSALPDDQLLTKGAQKGMGVA
VFNDNLRNALDGNVFDSSAQGFATGATGLTDAIKNGVEGSINDFTSSPGETINYVTSHDNYTLW
DKIALSNPNDSEADRIKMDELAQAVVMTSQGVPFMQGGEEMLRTKGGNDNSYNAGDAVNEFDWS
RKAQYPDVFNYYSGLIHLRLDHPAFRMTTANEINSHLQFLNSPENTVAYELTDHVNKDKWGNII
VVYNPNKTVATINLPSGKWAINATSGKVGESTLGQAEGSVQVPGISMMILHQEVSPDHGKK

FIGURE 8A

PULm104 nucleotide sequence
Bold = amyl signal sequence
Black = PULm104 mature coding sequence

**atgaaacaacaaaaacggctttacgcccgattgctgacgctgttatttgcgctcatcttcttgc
tgcctcattctgcagcttcagca**gctgctaaaccggcagtcagcaacgcttatctggatgccag
caaccaagtcctggtcaaactgagccaaccgctgacacttggagaaggagcgagcggatttacg
gtccatgatgacacggcgaacaaagatatcccggtcacgagcgttaaagatgctagcctgggcc
aagatgtcacagcagttctggcgggcacgtttaacatatctttggcggatcagattgggcacc
ggataatcacagcacgctgctgaaaaaagtcacgaacaacctgtatcagtttagcggagatctg
ccggaaggcaactatcaatataaagtcgcctgaacgatagctggaacaatccgagctatccga
gcgataacatcaatctgacagtcccggcaggcggagcacatgtcacgtttagctatatcccgag
cacacatgccgtctatgacacgatcaacaacccgaacgccgatcttcaagtcgaaagcggcgtc
aaaacggatctggtcacagtcacattgggagaagatccggatgtcagccatacactgagcatcc
aaacggatggctatcaagcgaaacaagtcatcccgagaaacgtcctgaacagcagccagtatta
ttatagcggcgatgatctgggcaacacgtatacacaaaaagcgacgacgtttaaagtttggcg
ccgacaagcacacaagtcaacgtcctgctgtatgattcagcaacaggcagcgtcacaaaaatcg
tcccgatgacagcatcaggacatggagtctgggaagcgacggtcaaccaaaacctggaaaactg
gtattatatgtatgaagtcacgggccaaggatcaacaagaacagcggtcgatccgtatgctaca
gcaatcgccccgaatggaacaagaggcatgatcgtcgatctggcaaaaacagacccggcaggct
ggaatagcgataaacatatcacgccgaaaaacatcgaagatgaagtcatctatgaaatggacgt
ccgggattttagcatcgatccgaacagcggcatgaaaaacaaaggcaaatatctggcgctgacg
gaaaaaggaacaaaaggcccggataacgtcaaaacaggcatcgatagcctgaaacaactgggca
tcacacatgtccaactgatgccggtctttgctagcaatagcgtcgatgaaacggacccgacaca
agataactggggctatgacccgagaaattatgatgtcccggaaggccaatatgccacgaacgcc
aatggaaacgcccggatcaaagaatttaaagaaatggtcctgagccttcatagagaacatatcg
gcgtcaacatggacgtcgtctataaccatacgtttgccacacagatcagcgactttgataaaat
cgtgccggaatattattatcggacggatgacgccggcaattatacgaatggcagcggcacagga
aatgaaatcgccgccgaaagaccgatggtccagaaatttatcatcgacagccttaaatattggg
tcaacgaatatcatatcgacggctttcgctttgatctgatggcgctgctgggcaaagatacaat
gagcaaagcggcgagcgaacttcatgctatcaatccgggcatcgctctttatggagaaccgtgg
acaggaggaacatcagcactgccggatgatcaactgctgacaaaaggcgcccaaaaaggaatgg
gagtcgccgtctttaacgacaacctgagaaatgccctggatggcaacgttttgatagcagcgc
ccaaggatttgctacaggagcgacaggactgacagatgccatcaaaaatggcgtcgaaggcagc
atcaacgattttacaagcagcccgggagagacgatcaattatgtcacgagccatgacaactata
cgctgtgggacaaaatcgctctgagcaacccgaatgatagcgaagcggaccggatcaaaatgga
tgaactggcacaagcagtcgtcatgacatcacaaggcgtcccgtttatgcaaggcggagaagaa
atgctgagaacgaaaggcggcaacgacaacagctataatgccggcgatgccgtcaatgaatttg
actggagccggaaagcacaatatccggacgtctttaactattattcaggacttatccatctgag
actggaccatccggcgtttagaatgacgacggcaacgaaatcaacagccatcttcagtttctg
aacagcccggaaaatacggtcgcctatgaactgacggaccatgtgaacaaagacaaatgggca
acatcatcgtcgtttataacccgaacaaaacggtcgccacaatcaatcttccgagcggcaaatg
ggcaatcaatgccacaagcggcaaagttggagaaagcacactgggacaagcagaaggatcagtc
caagtcccgggaatcagcatgatgatccttcatcaagaagtcagcccggaccacggcaaaaaa

FIGURE 8B

```
PULm104 protein sequence      (immature; SEQ ID NO: 4)
Bold = amyL signal sequence   (SEQ ID NO: 13)
Black = PULm104 mature sequence (SEQ ID NO: 14)
```

MKQQKRLYARLLTLLFALIFLLPHSAASAAKPAVSNAYLDASNQVLVKLSQPLTLGEGASGFT
VHDDTANKDIPVTSVKDASLGQDVTAVLAGTFQHIFGGSDWAPDNHSTLLKKVTNNLYQFSGDL
PEGNYQYKVALNDSWNNPSYPSDNINLTVPAGGAHVTFSYIPSTHAVYDTINNPNADLQVESGV
KTDLVTVTLGEDPDVSHTLSIQTDGYQAKQVIPRNVLNSSQYYYSGDDLGNTYTQKATTFKVWA
PTSTQVNVLLYDSATGSVTKIVPMTASGHGVWEATVNQNLENWYYMYEVTGQGSTRTAVDPYAT
AIAPNGTRGMIVDLAKTDPAGWNSDKHITPKNIEDEVIYEMDVRDFSIDPNSGMKNKGKYLALT
EKGTKGPDNVKTGIDSLKQLGITHVQLMPVFASNSVDETDPTQDNWGYDPRNYDVPEGQYATNA
NGNARIKEFKEMVLSLHREHIGVNMDVVYNHTFATQISDFDKIVPEYYYRTDDAGNYTNGSGTG
NEIAAERPMVQKFIIDSLKYWVNEYHIDGFRFDLMALLGKDTMSKAASELHAINPGIALYGEPW
TGGTSALPDDQLLTKGAQKGMGVAVFNDNLRNALDGNVFDSSAQGFATGATGLTDAIKNGVEGS
INDFTSSPGETINYVTSHDNYTLWDKIALSNPNDSEADRIKMDELAQAVVMTSQGVPFMQGGEE
MLRTKGGNDNSYNAGDAVNEFDWSRKAQYPDVFNYYSGLIHLRLDHPAFRMTTANEINSHLQFL
NSPENTVAYELTDHVNKDKWGNIIVVYNPNKTVATINLPSGKWAINATSGKVGESTLGQAEGSV
QVPGISMMILHQEVSPDHGKK

FIGURE 9A

PUL E99Q_E103Q nucleotide equence
Bold = amyL signal sequence
Black = PUL E99Q_E103Q mature coding sequence

**atgaaacaacaaaaacggctttacgcccgattgctgacgctgttatttgcgctcatcttcttgc
tgcctcattctgcagcttcagca**gatggcaatacgacgacgatcatcgtccattatttagacc
ggcgggagattatcaaccgtggagccttttggatgtggccgaaagatggaggaggagcggaatat
gattttaaccagccggcagattcacttggagcagtcgcctcagcagatattccgggaaatccga
gccaagtcggcatcatcgtcagaacacaggattggacgaaagatgtcagcgccgatcgctatat
cgatctgagcaaaggcaatgaagtctggctggtcgaaggcaacagccagatcttttatagcgaa
aaagacgccgaagatgctgctaaaccggcagtcagcaacgcttatctggatgccagcaaccaag
tcctggtcaaactgagccaaccgctgacacttggagaaggagcgagcggatttacggtccatga
tgacacggcgaacaaagatatcccggtcacgagcgttaaagatgctagcctgggccaagatgtc
acagcagttctggcgggcacgtttcaacatatctttggcggatcagattgggcaccggataatc
acagcacgctgctgaaaaaagtcacgaacaacctgtatcagtttagcggagatctgccggaagg
caactatcaatataaagtcgccctgaacgatagctggaacaatccgagctatccgagcgataac
atcaatctgacagtcccggcaggcggagcacatgtcacgtttagctatatcccgagcacacatg
ccgtctatgacacgatcaacaacccgaacgccgatcttcaagtcgaaagcggcgtcaaaacgga
tctggtcacagtcacattgggagaagatccggatgtcagccatacactgagcatccaaacggat
ggctatcaagcgaaacaagtcatcccgagaaacgtcctgaacagcagccagtattattatagcg
gcgatgatctgggcaacacgtatacacaaaaagcgacgacgtttaaagtttgggcgccgacaag
cacacaagtcaacgtcctgctgtatgattcagcaacaggcagcgtcacaaaaatcgtcccgatg
acagcatcaggacatggagtctgggaagcgacggtcaaccaaaacctggaaaactggtattata
tgtatgaagtcacgggccaaggatcaacaagaacagcggtcgatccgtatgctacagcaatcgc
cccgaatggaacaagaggcatgatcgtcgatctggcaaaaacagacccggcaggctggaatagc
gataaacatatcacgccgaaaaacatcgaagatgaagtcatctatgaaatggacgtccgggatt
ttagcatcgatccgaacagcggcatgaaaaacaaaggcaaatatctggcgctgacggaaaaagg
aacaaaaggcccggataacgtcaaaacaggcatcgatagcctgaaacaactgggcatcacacat
gtccaactgatgccggtctttgctagcaatagcgtcgatgaaacggacccgacacaagataact
ggggctatgacccgagaaattatgatgtcccggaaggccaatatgccacgaacgccaatggaaa
cgccccggatcaagaatttaaagaaatggtcctgagccttcatagagaacatatcggcgtcaac
atggacgtcgtctataaccatacgtttgccacacagatcagcgactttgataaaatcgtgccgg
aatattattcggacggatgacgccggcaattatacgaatggcagcggcacaggaaatgaaat
cgccgccgaaagaccgatggtccagaaatttatcatcgacagccttaaatattgggtcaacgaa
tatcatatcgacggctttcgctttgatctgatggcgctgctgggcaaagatacaatgagcaaag
cggcgagcgaacttcatgctatcaatccgggcatcgctctttatggagaaccgtggacaggagg
aacatcagcactgccggatgatcaactgctgacaaaaggcgcccaaaaaggaatgggagtcgcc
gtctttaacgacaacctgagaaatgccctggatggcaacgttttgatagcagcgcccaaggat
ttgctacaggagcgacaggactgacagatgccatcaaaaatggcgtcgaaggcagcatcaacga
ttttacaagcagcccgggagaaacgatcaattatgtcacgagccatgacaactatgctgtgg
gacaaaatcgctctgagcaacccgaatgatagcgaagcggaccggatcaaaatggatgaactgg
cacaagcagtcgtcatgacatcacaaggcgtcccgtttatgcaaggcggagaagaaatgctgag
aacgaaaggcggcaacgacaacagctataatgccggcgatgccgtcaatgaatttgactggagc
cggaaagcacaatatccggacgtctttaactattattcaggacttatccatctgagactggacc
atccggcgtttagaatgacgacggcgaacgaaatcaacagccatcttcagtttctgaacagccc
ggaaaatacggtcgcctatgaactgacggaccatgtgaacaaagacaaatggggcaacatcatc

FIGURE 9A (continued)

```
gtcgtttataacccgaacaaaacggtcgccacaatcaatcttccgagcggcaaatgggcaatca
atgccacaagcggcaaagttggagaaagcacactgggacaagcagaaggatcagtccaagtccc
gggaatcagcatgatgatccttcatcaagaagtcagcccggaccacggcaaaaaa
```

FIGURE 9B

PUL E99Q_E103Q protein sequence (immature; SEQ ID NO: 6)
Bold = amyL signal sequence (SEQ ID NO: 15)
Black = PUL E99Q_E103Q mature sequence (SEQ ID NO: 16)

MKQQKRLYARLLTLLFALIFLLPHSAASADGNTTTIIVHYFRPAGDYQPWSLWMWPKDGGGAEY
DFNQPADSLGAVASADIPGNPSQVGIIVRTQDWTKDVSADRYIDLSKGNEVWLVEGNSQIFYSQ
KDAQDAAKPAVSNAYLDASNQVLVKLSQPLTLGEGASGFTVHDDTANKDIPVTSVKDASLGQDV
TAVLAGTFQHIFGGSDWAPDNHSTLLKKVTNNLYQFSGDLPEGNYQYKVALNDSWNNPSYPSDN
INLTVPAGGAHVTFSYIPSTHAVYDTINNPNADLQVESGVKTDLVTVTLGEDPDVSHTLSIQTD
GYQAKQVIPRNVLNSSQYYYSGDDLGNTYTQKATTFKVWAPTSTQVNVLLYDSATGSVTKIVPM
TASGHGVWEATVNQNLENWYYMYEVTGQGSTRTAVDPYATAIAPNGTRGMIVDLAKTDPAGWNS
DKHITPKNIEDEVIYEMDVRDFSIDPNSGMKNKGKYLALTEKGTKGPDNVKTGIDSLKQLGITH
VQLMPVFASNSVDETDPTQDNWGYDPRNYDVPEGQYATNANGNARIKEFKEMVLSLHREHIGVN
MDVVYNHTFATQISDFDKIVPEYYYRTDDAGNYTNGSGTGNEIAAERPMVQKFIIDSLKYWVNE
YHIDGFRFDLMALLGKDTMSKAASELHAINPGIALYGEPWTGGTSALPDDQLLTKGAQKGMGVA
VFNDNLRNALDGNVFDSSAQGFATGATGLTDAIKNGVEGSINDFTSSPGETINYVTSHDNYTLW
DKIALSNPNDSEADRIKMDELAQAVVMTSQGVPFMQGGEEMLRTKGGNDNSYNAGDAVNEFDWS
RKAQYPDVFNYYSGLIHLRLDHPAFRMTTANEINSHLQFLNSPENTVAYELTDHVNKDKWGNII
VVYNPNKTVATINLPSGKWAINATSGKVGESTLGQAEGSVQVPGISMMILHQEVSPDHGKK

PULLULANASE VARIANTS WITH INCREASED PRODUCTIVITY

CROSS-REFERENCE TO RELATED APPLICATION

This application claims priority to U.S. Provisional Applications U.S. 60/903,247, filed Feb. 23, 2007 and U.S. 60/839,735, filed Aug. 23, 2006, each of which is herein incorporated by reference in its entirety.

FIELD OF THE INVENTION

The invention relates to novel variants of the enzymatic peptide pullulanase, the gene sequences encoding said novel peptides, expression vectors comprising those gene sequences as well as organisms expressing the novel pullulanase variants. Furthermore, the invention relates to the use of these novel pullulanase peptides in the textile, fermentation, food and other industries.

BACKGROUND OF THE INVENTION

Pullulanases are enzymes found useful in numerous industrial applications, especially in the food and beverage industries. Pullulanases are starch debranching enzymes and are effective in the debranching of starch hydrolyzates (useful in conditioning dough), the debranching of β-limit dextrans (useful in the brewing of beer and ales) and in the production of sugar syrups from corn, potato, wheat, manioc and rice, for example. Pullulanases are enzymes classified in EC 3.2.1.41 and such enzymes are characterized by their ability to hydrolyze the α-1,6-glycosidic bonds in, for example, amylopectin and pullulan.

Pullulanases are the product of bacteria, especially of the genus *Bacillus*. The production of pullulanases for industrial use is not without problems. Pullulanases are quickly degraded by various proteases also produced by the bacteria thereby making the recovery of large quantities of pullulanase inefficient and expensive. Various persons in the field have devised methods to increase production by limiting the degradation of pullulanase in the culture. For example, we have previously shown that deletion of the AprL and Mpr genes (which expressed proteases) from a pullulanase production strain was necessary for the economical expression of active pullulanase. Still, the fermentation time is limited to 51-60 hours to limit proteolytic degradation and activity loss of the pullulanase product. Svendsen has designed pullulanase variants that alter the three dimensional conformation of the enzyme to increase the thermal stability of the enzyme or to change how the enzyme degrades its substrate (see, U.S. Pat. Nos. 6,350,599 and 6,838,257 as well as US application no. 2004/0082028).

More recently, we have shown that the timing of pullulanase degradation was determined with the following result: between 30 and 50 hours a partial clipping of the full length pullulanase molecule into truncated molecules lacking the N-terminal 98 and 102 amino acids, respectively, was observed. Clipping occurred N-terminally of glutamic acid residues E99 and E103, respectively, and could be visualized by HPLC. Surprisingly, the 1-98 and 1-102 truncated pullulanase molecules retain pullulanase activity and even more surprising, it was demonstrated that this activity is higher than that of the full-length pullulanase. After 51 hours, further degradation of pullulanase molecules resulted in activity drop that eventually abolished all activity.

Still, there is room for improvement in the design of pullulanase peptides and the nucleotide seqeunces that encode them. Therefore, what is needed are compounds and methods for the more efficient production of pullulanase by, for example, limiting proteolytic degradation, increasing fermentation titers or increasing pullulanase activity.

SUMMARY OF THE INVENTION

The present invention relates to new and nonobvious forms of pullulanase, a peptide enzyme. The pullulanases of the present invention comprise novel modifications that result in superior performance in regard to production titers and/or withstanding degradation (e.g., enzymatic degradation by proteinases) and/or are more active in the breakdown of targeted substrate materials than the parent ("wild-type") peptides.

In this regard, the present invention relates to the pullulanases of peptide SEQ ID NO: 2, SEQ ID NO: 4 and SEQ ID NO: 6, as shown in FIGS. 7(*b*), 8(*b*) and 9(*b*), respectively. The present invention also relates to the nucleotide sequences encoding amino acid sequences SEQ ID NOS: 2, 4 and 6. The respective nucleotide sequences are also shown in FIGS. 7(*a*), 8(*a*) and 9(*a*) as SEQ ID NOS: 1, 3 and 5, respectively. As is well known in the art, the genetic code is redundant with multiple nucleotide codons encoding the same amino acid. Thus, the present invention additionally relates to any alternate nucleotide sequences that encode the peptides of SEQ ID NOS: 2, 4 and 6. One skilled in the art is able to determine the nucleotide sequences that encode the peptide sequences of the present invention based on the teachings of the specification and the knowledge in the art.

The present invention relates to expression constructs that encode the peptides of the present invention. The present invention is not limited to any specific expression construct as long as it is capable of the expression of the peptides of the present invention. In this regard, non-limiting examples of suitable expression constructs are shown schematically in part (a) of FIGS. 4-6.

As explained in greater detail in the Detailed Description and Examples sections of this specification, in one embodiment, the sequence encoding the parent pullulanase peptide (from *Bacillus deramificans*) was modified by codon-optimization techniques to produce a codon-optimized nucleotide sequence [SEQ ID NO: 1] encoding a duplicate of the wild-type (i.e., parent) pullulanase amino acid sequence [SEQ ID NO: 2]. The nucleotide sequence encoding amino acid sequence [SEQ ID NO: 2] was cloned in two orientations into the XhoI site of the *B. licheniformis* integration vector pICatH creating Ori1 (pICatH-PUL-Ori1) and Ori2 (pICatH-PUL-Ori2) versions of the expression construct.

In another embodiment, the sequence encoding the parent pullulanase peptide was modified to produce a pullulanase peptide from which the N-terminal 104 amino acids have been deleted. The nucleotide sequence encoding this novel pullulanase was also, in one embodiment, codon-optimized [SEQ ID NO: 3]. The peptide expressed by this construct, PULm104, is given in SEQ ID NO: 4 (See, FIG. 8(*b*)). The nucleotide sequence encoding [SEQ ID NO: 4] was cloned in two orientations into the XhoI site of the *B. licheniformis* integration vector pICatH creating Ori1 (pICatH-PULm104-Ori1) and Ori2 (pICatH-PULm104-Ori2) versions of the expression construct.

In another embodiment, the sequence encoding the parent pullulanase peptide was altered to replace the amino acid residues at positions 99 and 103 from glutamic acid (E) to glutamine (Q) to make the resultant peptide more resistant to proteolytic degradation at these positions. The nucleotide sequence encoding this novel pullulanase was also, in one embodiment, codon-optimized [SEQ ID NO: 5]. The peptide expressed by this nucleic acid sequence, PUL_E99Q_E103Q, is given in SEQ ID NO: 6. The nucleotide sequence encoding [SEQ ID NO: 6] was cloned in two orientations into the XhoI site of the *B. licheniformis* integration vector pICatH creating Ori1 (pICatH-PUL_E99Q_E103Q-Ori1) and Ori2 (pICat-PUL_E99Q_E103Q-Ori2) versions of the expression construct.

The present invention also relates to the transfection of the expression construct of the present invention into suitable host organisms. The present invention is not limited to any particular host organism. The host organism may be, for example, a microorganism, a eukaryotic cell or tissue culture, a plant cell or tissue culture or a fungal cell or tissue culture. In a preferred embodiment, the host organism in a microorganism. Preferred host organisms include, but are not limited to, *Bacillus* sp. (esp., *Bacillus subtilis, B. licheniformis* and *B. deramificicans*), *Escherichia coli, Trichoderma reesei, Saccharomyces cerevisiae* or *Aspergillus niger*. In a most preferred embodiment, the host organism is *B. licheniformis*.

The present invention relates to the isolation and purification of the peptides of the present invention from the medium in which the host organisms of the present invention are cultured. In this regard, the present invention is not limited to any particular isolation and purification technique so long as it results in a minimum purity of 10%. In a more preferred embodiment, the minimum purity of the isolated and purified peptide is 25%, in an even more preferred embodiment, the minimum purity of the isolated and purified peptide is 50%. In an even more preferred embodiment, the minimum purity of the isolated and purified peptide is 75%. In a most preferred embodiment, the minimum purity of the isolated and purified peptide of the present invention is 90%. Minimum purities may be measured by percent of total dry weight or other suitable means known in the art.

The present invention is not limited to any particular purification means of the isolation and purification of the peptides of the present invention. Any peptide purification means known in the art is suitable. Non-limiting examples of suitable purification means include affinity chromatography, precipitation, size exclusion chromatography, thin layer chromatography, electrophoresis, size filtration, etc.

One skilled in the art will recognize that a biologically active fragment of the pullulanases of the present invention may be used in lieu of the full-length sequence or equivalent in the context of the present invention. A "biologically active fragment" is intended to encompass any analogue, mimetic, truncation, deletion and/or substitution of the sequences of the present invention. Peptidomimetics of the pullulanases and active domains of the pullulanases of the present invention may be designed computationally using structural data, as is known in the art. Additionally, in one embodiment of the present invention, it is contemplated that analogs and mutations of the nucleotide sequences of the pullulanases of the present invention may be generated by directed molecular evolution. The techniques of directed molecular evolution are known in the art (see, for example, U.S. Pat. No. 5,605,793 to Stemmer, et al., or U.S. Pat. No. 6,537,776 to Short, which are incorporated herein by reference). The proteins generated by directed molecular evolution will have a lesser, greater or equal ability to function as a pullulanase as compared to the peptides of the present invention.

In another embodiment of the present invention, the peptides of the present invention are used as fusion proteins with, for example, other structural or functional peptide domains. Such domains may, for example, confer other enzymatic abilities to the fusion protein or tether the peptide to a surface.

Peptides of the invention also include those which arise as a result of the existence of multiple genes, alternative transcription events, alternative RNA splicing events, and alternative translational and posttranslational events. The polypeptide can be expressed in systems, e.g., cultured cells, which result in substantially the same posttranslational modifications present when expressed pullulanase is expressed in a native cell, or in systems which result in the omission of posttranslational modifications present when expressed in a native cell.

Also included in the invention is a composition which includes one or more pullulanase peptides (or a nucleic acid which encodes it) and one or more additional components, e.g., a carrier, diluent or solvent. The additional component can be one that renders the composition useful for in vitro, in vivo, pharmaceutical, or veterinary use.

In another aspect, the invention provides a substantially pure nucleic acid having or comprising a nucleotide sequence which encodes a polypeptide, the amino acid sequence of which includes, or is, the sequence of a pullulanase peptide of the present invention.

In preferred embodiments, the subject pullulanase nucleic acid will include a transcriptional regulatory sequence, e.g., at least one of a transcriptional promoter or transcriptional enhancer sequence, operably linked to the pullulanase gene sequence, e.g., to render the pullulanase gene sequence suitable for use as an expression vector.

In yet a further preferred embodiment, the nucleic acid which encodes a pullulanase peptide of the invention, hybridizes under stringent conditions to a nucleic acid probe corresponding to at least 12 consecutive nucleotides from SEQ ID NOS: 1, 3 or 5, more preferably to at least 20 consecutive nucleotides from SEQ ID NO: 1, 3 or 5.

Another preferred embodiment of the present invention provides for applications of pullulanase described herein in a variety of industrial settings. For example, the present invention relates to the use of the novel pullulanase variants of the invention in the production of food stuffs (including, but not limited to, various doughs and syrups), beverages (including and not limited to various brewed beverages such as beers and ales), bioethanol and numerous other products known to those practiced in the art.

BRIEF DESCRIPTION OF THE DRAWINGS

FIG. 1 shows a schematic representation of the current pullulanase process and the pullulanase variants designed in this project.

FIG. 7 shows (a) the nucleic acid sequence [SEQ ID NO: 1] and (b) the amino acid sequence [SEQ ID NO: 2] of codon-optimized immature "wild-type" pullulanase (PUL). The signal sequence is SEQ ID NO: 11 and the mature form of the PUL polypeptide is SEQ ID NO: 12.

FIG. 8 shows (a) the nucleic acid sequence [SEQ ID NO: 3] and (b) the amino acid sequence [SEQ ID NO: 4] of immature PULm104 pullulanase. The signal sequence is SEQ ID NO: 13 and the mature form of the PULm104 polypeptide is SEQ ID NO: 14. The signal sequence is SEQ ID NO: 11 and the mature form of the PUL polypeptide is SEQ ID NO: 12.

FIG. 9 shows (a) the nucleic acid sequence [SEQ ID NO: 5] and (b) the amino acid sequence [SEQ ID NO: 6] of immature PUL_E99Q_E103Q pullulanase. The signal sequence is SEQ ID NO: 15 and the mature form of the PUL_E99Q_E103Q polypeptide is SEQ ID NO: 16.

DEFINITION SECTION

Figure 2:
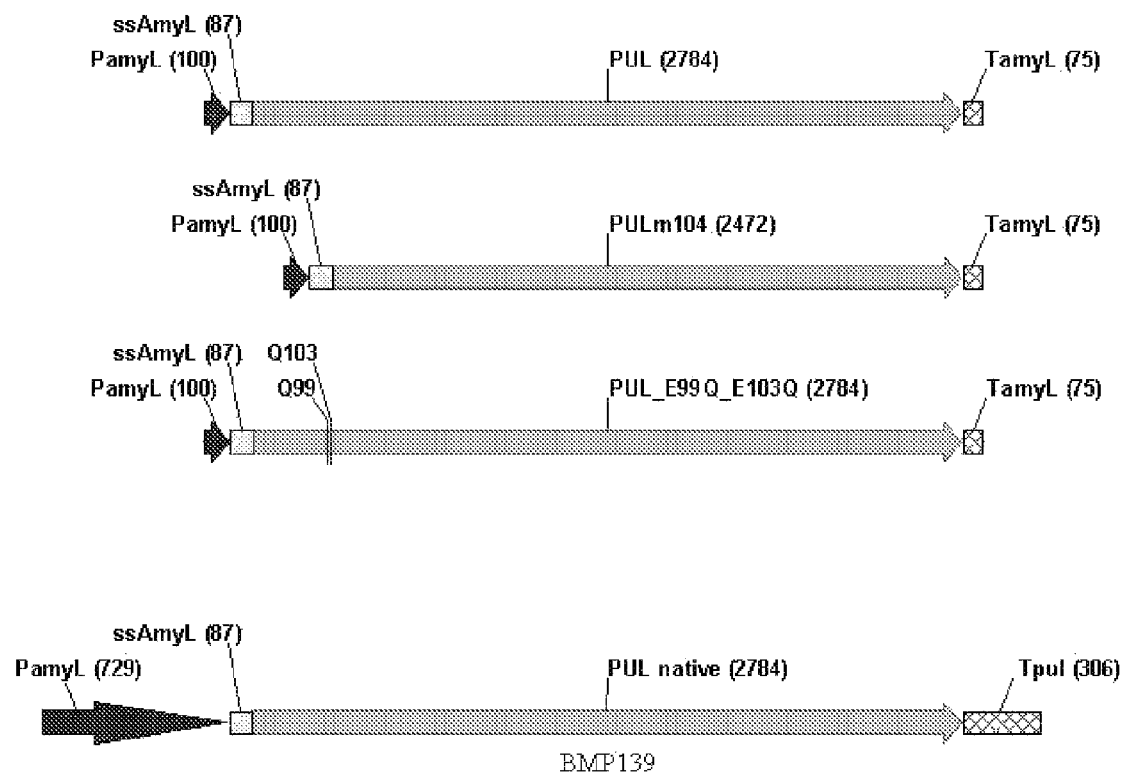
FIG. 2 shows the molecular architecture of the constructions present in the pullulanase expression strains made in the current invention, in comparison to the pullulanase expression construction in strain BMP139.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The term "pullulanase" refers to a specific kind of glucanase, an amylolytic endoenzyme that degrades pullulan. It is produced as, for example, an extracellular, cell surface-anchored lipoprotein by Gram-negative bacteria of the genus *Klebsiella*. Gram-positive bacteria, however, produce pullulanases as secreted proteins. Type I pullulanases specifically attack α-1,6 linkages, while type II pullulanases are also able to hydrolyse α-1,4 linkages. It is also produced by some other bacteria and archaea. Pullulanase is used as a detergent in biotechnology. Pullulanase (EC 3.2.1.41) is also known as pullulan-6-glucanohydrolase (debranching enzyme). Pullulan is regarded as a chain of maltotriose units linked by α-1,6-glucosidic bonds. Pullulanase will hydrolytically cleave pullulan α-glucan polysaccharides).

The term "codon optimization" refers to techniques to enhance expression levels by replacing nucleotide codons in a coding sequence with codons that code for the same amino acid but are more efficiently processed by the host organism. Codon preference among different species could be dramatically different. To enhance the expression level of a foreign protein in a particular expression system (bacteria, fungi, yeast, insect, plant or mammalian cells), it is very important to adjust the codon frequency of the foreign protein to match that of the host expression system. One classic example is GFP (green fluorescent protein) which was optimized to achieve high-level of expression in mammalian cells. Thus, codon-optimization may be used to express the proteins of the present invention in a wide variety of host organisms where such sequences might not be expressed efficiently if at all.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes include a promoter, optionally an operator sequence, a ribosome binding site and possibly other sequences.

A "heterologous promoter," as used herein, is a promoter which is not naturally associated with a gene or a purified nucleic acid. The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

The term "cell-type specific" or "host organism specific" or equivalent terms as applied to a regulatory element refers to a regulatory element which is capable of directing selective expression of a nucleotide sequence of interest in a specific type of cell or organism in the relative absence of expression of the same nucleotide sequence of interest in a different type of cell or organism within the same tissue. The term "cell-type specific" or "host organism specific" when applied to a regulatory element also means a regulatory element capable of promoting selective expression of a nucleotide sequence of interest in a region within a single tissue or organism, respectively.

An "isolated," "purified preparation" or a "substantially pure preparation" of a polypeptide, as used herein, means a polypeptide that has been identified and separated from at least one contaminant with which it is ordinarily associated in its natural state, or when obtained from its actual source. The at least one other contaminant may be, for example, other proteins, lipids, and nucleic acids with which it naturally occurs. Preferably, the polypeptide is also separated from substances, e.g., antibodies or gel matrix, e.g., polyacrylamide, which are used to purify it. Preferably, the polypeptide constitutes at least 10, 20, 50 70, 80 or 95% dry weight of the purified preparation. Preferably, the preparation contains: sufficient polypeptide to allow protein sequencing; at least 1, 10, or 100 mg of the polypeptide; at least 1, 10, or 100 mg of the polypeptide.

A "purified preparation of cells," as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

A "substantially pure nucleic acid," e.g., a substantially pure DNA, is a nucleic acid which is one or both of: not immediately contiguous with either one or both of the sequences, e.g., coding sequences, with which it is immediately contiguous (i.e., one at the 5' end and one at the 3' end) in the naturally-occurring genome of the organism from which the nucleic acid is derived; or which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Additionally, the term "isolated" when used in relation to a nucleic acid, as in "an isolated nucleic acid sequence" refers to a nucleic acid sequence that is identified and separated from at least one contaminant nucleic acid with which it is ordinarily associated in its natural state, or when obtained from its actual source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, an isolated nucleic acid sequence comprising, for example, SEQ ID NO: 1 includes, by way of example, such nucleic acid sequences in cells which ordinarily contain SEQ ID NO: 1 where the nucleic acid sequence is in a chromosomal or extrachromosomal location different from that of natural cells, or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain (at a minimum) at least a portion of the sense or coding strand (i.e., the nucleic acid sequence may be single-stranded). Alternatively, it may contain both the sense and anti-sense strands (i.e., the nucleic acid sequence may be double-stranded).

"Homologous," as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10, of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The terms "peptide(s)," "protein(s)" and "polypeptide(s)" are used interchangeably herein.

The term "protease" means a protein or polypeptide domain of a protein or polypeptide derived from a microorganism, e.g., a fungus, bacterium, or from a plant or animal, and that has the ability to catalyze cleavage of peptide bonds at one or more of various positions of a protein backbone.

Preferably, pullulanase proteins according to the present invention are isolated or purified. By purification or isolation is meant the pullulanase protein is altered from its natural state by virtue of separating the pullulanase from some or all of the naturally occurring constituents with which it is associated in nature. Such isolation or purification may be accomplished by art recognized separation techniques such as ion exchange chromatography, affinity chromatography, hydrophobic separation, dialysis, protease treatment, ammonium sulphate precipitation or other protein salt precipitation, centrifugation, size exclusion chromatography, filtration, microfiltration, gel electrophoresis or separation on a gradient to remove whole cells, cell debris, impurities, extraneous proteins, or enzymes undesired in the final composition. It is further possible to then add constituents to the pullulanase containing composition which provide additional benefits, for example, activating agents, anti-inhibition agents, desirable ions, compounds to control pH or other enzymes. Preferably, pullulanase proteins according to the present invention are produced by recombinant methods.

As used herein, "microorganism" refers to a bacterium, a fungus, a virus, a protozoan and other microbes or microscopic organisms. In the present invention, microorganisms are used as host organisms for the expression of exogenous peptides.

As used herein, "derivative," "variant" or "modified peptide, polypeptide or protein" means a protein which is derived from a precursor protein (e.g., the native protein) by addition of one or more amino acids to either or both the C- and N-terminal end, substitution of one or more amino acids at one or a number of different sites in the amino acid sequence, deletion of one or more amino acids at either or both ends of the protein or at one or more sites in the amino acid sequence, or insertion of one or more amino acids at one or more sites in the amino acid sequence. The preparation of a pullulanase derivative is preferably achieved by modifying a DNA sequence which encodes the native protein, transformation of that DNA sequence into a suitable host, and expression of the modified DNA sequence to form the derivative pullulanase. "Derivatives" of the invention include peptides including altered amino acid sequences in comparison with a precursor amino acid sequence (e.g., a wild type or native state pullulanase), wherein the peptides retain a characteristic pullulanase nature of the precursor pullulanase but have altered properties in some specific aspect. For example, a pullulanase derivative may have an increased pH optimum, increased resistance to enzymatic degradation or other degradation, increased enzymatic effectiveness, increased temperature or oxidative stability but retains its characteristic enzymatic modification activity. Similarly, derivatives according to the present invention includes a protein, or other substrate, binding domain, which has been added or modified to alter its substrate binding ability. It is contemplated that derivatives according to the present invention are derived from a DNA fragment encoding a pullulanase derivative wherein the functional activity of the expressed pullulanase derivative is retained. Derivatives farther include chemical modifications that change the characteristics of the pullulanase.

Ordinarily, a pullulanase derivative will have at least about 50%, 70% or 85% amino acid sequence identity, preferably at least about 85% amino acid sequence identity, more preferably at least about 90% amino acid sequence identity, even more preferably at least about 95% amino acid sequence identity and yet more preferably 98% amino acid sequence identity. Preferably, any amino acid substitutions are "conservative amino acid substitutions" using L-amino acids, wherein one amino acid is replaced by another biologically similar amino acid. Conservative amino acid substitutions are those that preserve the general charge, hydrophobicity/hydrophilicity, and/or steric bulk of the amino acid being substituted. Examples of conservative substitutions are those between the following groups: Gly/Ala, Val/Ile/Leu, Lys/Arg, Asn/Gln, Glu/Asp, Ser/Cys/Thr, and Phe/Trp/Tyr. A derivative may, for example, differ by as few as 1 to 10 amino acid residues, such as 6-10, as few as 5, as few as 4, 3, 2, or even 1 amino acid residue. Table 1 herein illustrates exemplary amino acid substitutions that are recognized in the art.

As used herein, a "native sequence" of pullulanase or a "wild-type" sequence of pullulanase includes a polypeptide having the same amino acid sequence as a pullulanase derived from the parent strain of nature or the same amino acid sequence as the pullulanase from which the modified or derived pullulanase was made, e.g., the pullulanase expressed by the parent strain *B. deramificans* (BMP139) of the present invention. Such a native sequence pullulanase can be isolated from nature or can be produced by recombinant or synthetic means. The term "wild-type" or "native sequence" pullulanase, in one embodiment, refers to the pullulanase peptide from which the variants of the present invention were derived and is found in FIG. 7b as SEQ ID NO: 2.

As used herein, "percent (%) sequence identity" with respect to the amino acid or nucleotides sequences identified herein is defined as the percentage of amino acid residues or nucleotides in a candidate sequence that are identical with the amino acid residues or nucleotides in a pullulanase sequence, after aligning the sequences and introducing gaps, if necessary, to achieve the maximum percent sequence identity, and not considering any conservative substitutions as part of the sequence identity. Methods for performing sequence alignment and determining sequence identity are known to the skilled artisan, may be performed without undue experimentation, and calculations of identity values may be obtained with definiteness. See, for example, Ausubel, et al., eds. (1995) Current Protocols in Molecular Biology, Chapter 19 (Greene Publishing and Wiley-Interscience, New York); and the ALIGN program (Dayhoff (1978) in Atlas of Protein Sequence and Structure 5:Suppl. 3 (National Biomedical Research Foundation, Washington, D.C.). A number of algorithms are available for aligning sequences and determining sequence identity and include, for example, the homology alignment algorithm of Needleman et al. (1970) J. Mol. Biol. 48:443; the local homology algorithm of Smith, et al. (1981) Adv. Appl. Math. 2:482; the search for similarity method of Pearson, et al. (1988) Proc. Natl. Acad. Sci. 85:2444; the Smith-Waterman algorithm (Meth. Mol. Biol. 70:173-187 (1997); and BLASTP, BLASTN, and BLASTX algorithms (see Altschul, et al. (1990) J. Mol. Biol. 215:403-410). Computerized programs using these algorithms are also available, and include, but are not limited to: ALIGN or Megalign (DNASTAR) software, or WU-BLAST-2 (Altschul, et al., Meth. Enzym., 266:460-480 (1996)); or GAP, BESTFIT, BLAST (Altschul, et al), supra, FASTA, and TFASTA, available in the Genetics Computing Group (GCG) package, Version 8, Madison, Wis., USA; and CLUSTAL in the PC/Gene program by Intelligenetics, Mountain View, Calif. Those skilled in the art can determine appropriate parameters for measuring alignment, including algorithms needed to achieve maximal alignment over the length of the sequences being compared. Preferably, the sequence identity is determined using the default parameters determined by the program. Specifically, sequence identity can be determined by the Smith-Waterman homology search algorithm (Meth. Mol. Biol. 70:173-187 (1997)) as implemented in MSPRCH program (Oxford Molecular) using an affine gap search with the following search parameters: gap open penalty of 12, and gap extension penalty of 1. Preferably, paired amino acid comparisons can be carried out using the GAP program of the GCG sequence analysis software package of Genetics Computer Group, Inc., Madison, Wis., employing the blosum62 amino acid substitution matrix, with a gap weight of 12 and a length weight of 2. With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues, and may be 30, 40, 50, or more amino acid residues. Corrections for increased sequence identity associated with inclusion of gaps in the derivative's amino acid sequence can be made by assigning gap penalties.

As used herein, "expression construct" (or "expression vector") means a DNA construct including a DNA sequence which is operably linked to a suitable control sequence capable of affecting the expression of the DNA in a suitable host. Such control sequences may include a promoter to affect transcription, an optional operator sequence to control transcription, a sequence encoding suitable ribosome-binding sites on the mRNA, and sequences which control termination of transcription and translation. The present invention is not limited to the use of any particular expression construct. Different cell types are preferably used with different expression vectors. For example, a preferred promoter for vectors used in *Bacillus subtilis* is the AprE promoter; a preferred promoter for vectors used in *Bacillus deramificans* is the amyL promoter; a preferred promoter used in *E. coli* is the Lac promoter, a preferred promoter used in *Saccharomyces cerevisiae* is PGK1, a preferred promoter used in *Aspergillus niger* is glaA and a preferred promoter for *Trichoderma reesei* is cbhI. The vector may be a plasmid, a phage particle, or simply a potential genomic insert.

Once transformed (or, transfected) into a suitable host, the expression construct may replicate and function independently of the host genome or, may, under suitable conditions, integrate into the genome itself. In the present specification, the terms "plasmid," "vector" and "expression construct(s)" are sometimes used interchangeably. However, the invention is intended to include other forms of expression vectors which serve equivalent functions and which are, or become, known in the art. Thus, a wide variety of host/expression vector combinations may be employed in expressing the DNA sequences of this invention. Useful expression vectors for the present invention not touched upon elsewhere in this specification, for example, may consist of segments of chromosomal, non-chromosomal and synthetic DNA sequences such as various known derivatives of SV40 and known bacterial plasmids, e.g., plasmids from *E. coli* including col E1, pCR1, pBR322, pMb9, pUC 19 and their derivatives, wider host range plasmids, e.g., RP4, phage DNAs, e.g., the numerous derivatives of phage λ, e.g., NM989, other DNA phages, e.g., M13 and filamentous single stranded DNA phages, yeast plasmids such as the 2υ plasmid or derivatives thereof, vectors useful in eukaryotic cells, such as vectors useful in animal cells and vectors derived from combinations of plasmids and phage DNAs, such as plasmids which have been modified to employ phage DNA or other expression control sequences.

Expression techniques using the expression vectors of the present invention are known in the art and are described generally in, for example, Sambrook, et al., MOLECULAR CLONING: A LABORATORY MANUAL, SECOND EDITION, Cold Spring Harbor Press (1989). Often, such expression vectors including the DNA sequences of the invention are transformed into a unicellular host by direct insertion into the genome of a particular species through an integration event (see, e.g., Bennett & Lasure, MORE GENE MANIPULATIONS IN FUNGI, Academic Press, San Diego, pp. 70-76 (1991) and articles cited therein describing targeted genomic insertion in fungal hosts).

The terms "operably linked," "in operable combination," and "in operable order" as used herein refer to the linkage of nucleic acid sequences such that they perform their intended function. For example, operably linking a promoter sequence to a nucleotide sequence of interest refers to linking the promoter sequence and the nucleotide sequence of interest in a manner such that the promoter sequence is capable of directing the transcription of the nucleotide sequence of interest and/or the synthesis of a polypeptide encoded by the nucleotide sequence of interest. Similarly, operably linking a nucleic acid sequence having age-related regulatory activity to a promoter sequence and to a nucleotide sequence of interest means linking the nucleic acid sequence having age-related regulatory activity, the promoter sequence and the nucleotide sequence of interest in a manner such that the nucleic acid sequence having age-related regulatory activity is capable of altering over a period of time the level of transcription into mRNA of the nucleotide sequence of interest and/or the synthesis of a polypeptide encoded by the nucleotide sequence of interest.

As used herein, "host organism," "host strain" or "host cell" means a suitable host for an expression vector including DNA according to the present invention. Host cells useful in the present invention are generally prokaryotic or eukaryotic hosts, including any transformable microorganism in which expression can be achieved. In the context of the present invention, for example, host strains may be *Bacillus subtilis, Bacillus deramificans* (or other *Bacillus* sp.) *Escherichia coli, Trichoderma reesei, Saccharomyces cerevisiae* or *Aspergillus niger*. Host cells are transformed or transfected with vectors constructed using recombinant DNA techniques. Such transformed host cells may be capable of both replicating vectors encoding pullulanase and its derivatives or variants (mutants) or expressing the desired peptide product or both.

The term "culture" or "culture conditon(s)," when used in the context of growing a population of host organisms, refers to a culture vessel, culture medium and culture conditions that are suitable for the growth of the host organism and, in the case of host organisms transfected with the nucleotide sequences of the present invention and their variants, for the production of the pullulanases of the present invention. The present invention is not limited to any particular culture or culture condition as long as the forgoing is satisfied.

As used herein, "functionally attached" or "operably linked" means that a regulatory region, such as a promoter, terminator, secretion signal or enhancer region is attached to or linked to a structural gene and controls the expression of that gene.

As used herein, a substance (e.g., a polynucleotide or protein) "derived from" a microorganism means that the substance is native to the microorganism.

"*Trichoderma*" or "*Trichoderma* sp." refers to any fungal strains which have previously been classified as *Trichoderma* or which are currently classified as *Trichoderma*. Preferably the species are *Trichoderma longibrachiatum, Trichoderma reesei* or *Trichoderma viride*. In the present invention, *Trichoderma* sp. May be used as a host organism in the present invention.

As described herein, one aspect of the invention features a "substantially pure" (or recombinant) nucleic acid which includes a nucleotide sequence encoding a pullulanase polypeptide and/or equivalents of such nucleic acids. The term nucleic acid as used herein can include fragments and equivalents. The term "equivalent" refers to nucleotide sequences encoding functionally equivalent polypeptides or functionally equivalent proteins. Equivalent nucleotide sequences will include sequences that differ by one or more nucleotide substitutions, additions or deletions, such as allelic variants, and include sequences that differ from the nucleotide sequence of pullulanase shown in SEQ ID NO: 1, due to the degeneracy of the genetic code.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. All publications, patents and patent applications cited herein are hereby incorporated by reference in their entirety for all purposes. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu, et al., eds.), *Immunochemical Methods In Cell And Molecular Biology* (Mayer and Walker, eds., Academic Press, London, 1987); *Handbook Of Experimental Immunology,* Volumes I-IV (D. M. Weir and C. C. Blackwell, eds., 1986); *Manipulating the Mouse Embryo,* (Cold Spring Harbor Laboratory Press, Cold Spring Harbor, N.Y., 1986). Also, information regarding methods of preparation, expression, isolation and use of proteases may be obtained by review of U.S. Pat. No. 6,768,001, which is herein, in its entirety, incorporated by reference.

Other features and advantages of the invention will be apparent from the following detailed description, and from the claims.

DETAILED DESCRIPTION

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

Numeric ranges are inclusive of the numbers defining the range.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

Molecular Biology

In one embodiment this invention provides for the expression of heterologous genes under control of the amyL promoter. Therefore, this invention relies on routine techniques in the field of recombinant genetics. Basic texts disclosing the general methods of use in this invention include Sambrook, et al., Molecular Cloning, A Laboratory Manual (2nd ed. 1989); Kriegler, Gene Transfer and Expression: A Laboratory Manual (1990); and Ausubel, et al., eds., Current Protocols in Molecular Biology (1994)).

Heterologous genes comprising the cellulase gene promoter sequences of filamentous fungi are typically cloned into intermediate vectors before transformation into *Trichoderma reesei* cells for replication and/or expression. These intermediate vectors are typically prokaryotic vectors, e.g., plasmids, or shuttle vectors.

To obtain high level expression of a cloned gene, the heterologous gene is preferably positioned about the same distance from the promoter as is in the naturally occurring cellulase gene. As is known in the art, however, some variation in this distance can be accommodated without loss of promoter function.

Those skilled in the art are aware that a natural promoter can be modified by replacement, substitution, addition or elimination of one or more nucleotides without changing its function. The practice of the invention encompasses and is not constrained by such alterations to the promoter.

The expression vector/construct typically contains a transcription unit or expression cassette that contains all the additional elements required for the expression of the heterologous sequence. A typical expression cassette thus contains a promoter operably linked to the heterologous nucleic acid sequence and signals required for efficient polyadenylation of the transcript, ribosome binding sites, and translation termination. Additional elements of the cassette may include enhancers and, if genomic DNA is used as the structural gene, introns with functional splice donor and acceptor sites.

The practice of the invention is not constrained by the choice of promoter in the genetic construct. However, exemplary promoters are the *Trichoderma reesei* cbh1, cbh2, eg1, eg2, eg3, eg5, xln1 and xln2 promoters.

In addition to a promoter sequence, the expression cassette should also contain a transcription termination region downstream of the structural gene to provide for efficient termination. The termination region may be obtained from the same gene as the promoter sequence or may be obtained from different genes.

Although any fungal terminator is likely to be functional in the present invention, preferred terminators include: the terminator from *Aspergillus nidulans* trpC gene (Yelton, M. et al. (1984) PNAS USA 81:1470-1474, Mullaney, E. J. et al. (1985) MGG 199:37-45), the *Aspergillus awamori* or *Aspergillus niger* glucoamylase genes (Nunberg, J. H. et al. (1984) Mol. Cell. Biol. 4:2306, Boel, E. et al. (1984) EMBO J. 3:1581-1585) and the *Mucor miehei* carboxyl protease gene (EPO Publication No. 0 215 594).

The particular expression vector used to transport the genetic information into the cell is not particularly critical. Any of the conventional vectors used for expression in eukaryotic or prokaryotic cells may be used. Standard bacterial expression vectors include bacteriophages λ and M13, as well as plasmids such as pBR322-based plasmids, pSKF, pET23D, and fusion expression systems such as MBP, GST, and LacZ. Epitope tags can also be added to recombinant proteins to provide convenient methods of isolation, e.g., c-myc.

The elements that are typically included in expression vectors also include a replicon, a gene encoding antibiotic resistance to permit selection of bacteria that harbor recombinant plasmids, and unique restriction sites in nonessential regions of the plasmid to allow insertion of heterologous sequences. The particular antibiotic resistance gene chosen is not critical, any of the many resistance genes known in the art are suitable. The prokaryotic sequences are preferably chosen such that they do not interfere with the replication or integration of the DNA in *Trichoderma reesei*.

The methods of transformation of the present invention may result in the stable integration of all or part of the transformation vector into the genome of the filamentous fungus. However, transformation resulting in the maintenance of a self-replicating extra-chromosomal transformation vector is also contemplated.

Many standard transfection methods can be used to produce *Trichoderma reesei* cell lines that express large quantities of the heterologous protein. Some of the published methods for the introduction of DNA constructs into cellulase-producing strains of *Trichoderma* include Lorito, Hayes, DiPietro and Harman, 1993, Curr. Genet. 24: 349-356; Goldman, VanMontagu and Herrera-Estrella, 1990, Curr. Genet. 17:169-174; Penttila, Nevalainen, Ratto, Salminen and Knowles, 1987, Gene 6: 155-164, for *Aspergillus*, Yelton, Hamer and Timberlake, 1984, Proc. Natl. Acad. Sci. USA 81: 1470-1474, for *Fusarium* Bajar, Podila and Kolattukudy, 1991, Proc. Natl. Acad. Sci. USA 88: 8202-8212, for *Streptomyces* Hopwood et al., 1985, The John Innes Foundation, Norwich, UK and for *Bacillus* Brigidi, DeRossi, Bertarini, Riccardi and Matteuzzi, 1990, FEMS Microbiol. Lett. 55: 135-138).

However, any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). Also of use is the *Agrobacterium*-mediated transfection method described in U.S. Pat. No. 6,255,115. It is only necessary that the particular genetic engineering procedure used be capable of successfully introducing at least one gene into the host cell capable of expressing the heterologous gene.

The invention also relates to a pullulanase produced heterologously by a microorganism. Examples of suitable bacteria are gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis*, or *Streptomyces lividans* or *Streptomyces murinus*, or gram negative bacteria such as *E. coli*. The transformation of the bacteria may, for instance, be effected by protoplast transformation or by using competent cells in a manner known per se.

Generally, the present invention includes a method for producing a pullulanase by expressing the DNA incorporated in an expression system which has been transformed into a host cell. A wide variety of host/expression vector combinations may be employed in expressing the DNA sequences of this invention. Many prokaryotic and eukaryotic expression vectors are commercially available. Selection of appropriate expression vectors is within the knowledge of those having skill in the art. The vector may be a plasmid, a phage particle, or simply a potential genomic insert. Once transformed into a suitable host, the vector may replicate and function independently of the host genome, or may, in some instances, integrate into the genome itself. In the present specification, plasmid and vector are sometimes used interchangeably as the plasmid is the most commonly used form of vector at present. However, the invention is intended to include such other forms of expression vectors which serve equivalent functions and which are, or become, known in the art. Useful expression vectors, for example, include segments of chromosomal, non-chromosomal and synthetic DNA sequences, such as the various known plasmids and phages useful for this purpose. In addition, any of a wide variety of expression control sequences are generally used in these vectors.

Host cells useful in the present invention are generally procaryotic or eucaryotic hosts, including any transformable microorganism in which the expression of pullulanase according to the present invention can be achieved. Host cells are transformed or transfected with vectors constructed using recombinant DNA techniques. Such transformed host cells are capable of either replicating vectors encoding the pullulanase and its variants (mutants) or expressing the desired pullulanase. These hosts may include well known eukaryotic and prokaryotic hosts, such as strains of *E. coli, Pseudomonas, Bacillus, Streptomyces*, various fungi, yeast and animal cells. Preferably, the host expresses the pullulanase of the present invention extracellularly to facilitate purification and downstream processing.

In some embodiments, the host cell is a member of the genus *Bacillus*, while in some embodiments, the *Bacillus* strain of interest in an industrial *Bacillus* strain. Examples of industrial *Bacillus* strains include, but are not limited to *B. licheniformis, B. subtilis, B lentus, B amyloliquefaciens*. In additional embodiments, the *Bacillus* host strain is selected from the group consisting of *B. lentus, B. brevis, B. stearothermophilus, B. alkalophilus, B. coagulans, B. cirulans, B. pumilus, B. thuringiensis, B. clausii*, and *B. megaterium*, as well as as other organisms within the genus *Bacillus*, as discussed above. In some embodiments, *B. subtilis* is used. In other embodiments, *B. licheniformis* is used. For example, U.S. Pat. Nos. 5,264,366 and 4,760,025 (RE34,606), and US2002/0182734 (International Publication No. WO 02/14490) describe various *Bacillus* host strains that find use in the present invention, although other suitable strains are contemplated for use in the present invention. Preferably, a protease negative *Bacillus* strain (genes deleted, e.g., Δapr or Δnpr among others) is used.

Various methods are known for the transformation of *Bacillus* species. Indeed, methods for altering the chromosome of *Bacillus* involving plasmid constructs and transformation of the plasmids into *E. coli* are well known. In most methods, plasmids are subsequently isolated from *E. coli* and transformed into *Bacillus*. However, it is not essential to use such intervening microorganism such as *E. coli* and in some embodiments, the DNA construct is directly transformed into a competent *Bacillus* host via protoplasts or competent cell transformation. Expression and purification of the mutant pullulanase of the invention may be effected through art-recognized means for carrying out such processes.

After the expression vector is introduced into the cells, the transfected cells are cultured under conditions favoring expression of genes under control of protease gene promoter sequences. Large batches of transformed cells can be cultured as described in the Examples, infra. Finally, product is recovered from the culture using standard techniques.

Thus, the invention herein provides for the expression and enhanced secretion of desired polypeptides whose expression is under control of gene promoter sequences including naturally occurring amylase genes, fusion DNA sequences, and various heterologous constructs. The invention also provides processes for expressing and secreting high levels of such desired polypeptides.

Protein Expression

Proteins of the present invention are produced by culturing cells transformed with an expression vector containing genes whose expression is under control of amylase gene promoter sequences. The present invention is particularly useful for enhancing the intracellular and/or extracellular production of proteins. The protein may be homologous or heterologous. Proteins that may be produced by the instant invention include, but are not limited to, hormones, enzymes, growth factors, cytokines, antibodies and the like.

Enzymes include, but are not limited to, hydrolases, such as protease, esterase, lipase, phenol oxidase, permease, amylase, pullulanase, cellulase, glucose isomerase, laccase and protein disulfide isomerase.

Conditions appropriate for expression of said genes comprise providing to the culture an inducing feed composition, see, for example, US-2004-0121446. Optimal conditions for the production of the proteins will vary with the choice of the host cell, and with the choice of protein to be expressed. Such conditions will be easily ascertained by one skilled in the art through routine experimentation or optimization.

The protein of interest, e.g., a pullulanase as described herein, is typically purified or isolated after expression. The protein of interest may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the protein of interest may be purified using a standard antiprotein of interest antibody column. Ultrafiltration and diafiltration techniques, in conjunction with protein concentration, are also useful. For general guidance in suitable purification techniques, see Scopes, Protein Purification (1982). The degree of purification necessary will vary depending on the use of the protein of interest. In some instances no purification will be necessary.

Analogs of the Pullulanases of the Present Invention

Analogs can differ from the "wild-type" parent pullulanase or from a naturally occurring pullulanase in amino acid sequence or in ways that do not involve sequence, or both. Non-sequence modifications include in vivo or in vitro chemical derivatization of pullulanase. Non-sequence modifications include changes in acetylation, methylation, phosphorylation, carboxylation, or glycosylation.

Preferred analogs include pullulanase (or biologically active fragments thereof) whose sequences differ from the "wild-type" sequence or from the natural sequence by one or more conservative amino acid substitutions or by one or more non-conservative amino acid substitutions, deletions, or insertions which do not abolish the pullulanase biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine.

Conservative substitutions may be made, for example according to the table below which describes a generally accepted Venn diagram grouping of amino acids.

TABLE 1

| Set | | Sub-set | |
|---|---|---|---|
| Hydrophobic | FWYHKMILVAGC | Aromatic | FWYH |
| | | Aliphatic | ILV |
| Polar | WYHKREDCSTNQ | Charged | HKRED |
| | | Positively charged | HKR |
| | | Negatively charged | ED |
| Small | VCAGSPTND | Tiny | AGS |

Other conservative substitutions can be taken from the table below.

TABLE 2

CONSERVATIVE AMINO ACTD REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, b-Ala Acp |
| Isoleucine | I | D-Ile, Val, D-Val, Leu, D-Leu, Met, D-Met |
| Leucine | L | D-Leu, Val, D-Val, Ile, D-Ile, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Tyr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., $\alpha$ or $\beta$ amino acids analogs and cyclic analogs.

Other Embodiments

Included in the invention are: allelic variations; natural mutants; induced mutants; proteins encoded by DNA that hybridizes under high or low stringency conditions to a nucleic acid which encodes a polypeptide of SEQ ID NO: 1 (for definitions of high and low stringency see Current Protocols in Molecular Biology, John Wiley & Sons, New York, 1989, 6.3.1-6.3.6, hereby incorporated by reference); and polypeptides specifically bound by antisera to pullulanase, especially by antisera to an active site or binding domain of pullulanase.

Nucleic acids and polypeptides of the invention include those that differ from the sequences disclosed herein by virtue of sequencing errors in the disclosed sequences.

The invention also includes fragments, preferably biologically active fragments or analogs of pullulanase. A biologically active fragment or analog is one having any in vivo or in vitro activity which is characteristic of the pullulanase shown in SEQ ID NOS: 2, 4 and 6 or of other naturally occurring pullulanases, e.g., one or more of the biological activities described herein. Especially preferred are fragments which exist in vivo, e.g., fragments which arise from posttranscriptional processing or which arise from translation of alternatively spliced RNA's. Fragments include those expressed in native or endogenous cells, e.g., as a result of post-translational processing, e.g., as the result of the removal of an amino-terminal signal sequence as well as those made in expression systems, e.g., in CHO cells. Particularly preferred fragments are fragments, e.g., active fragments, which are generated by proteolytic cleavage or alternative splicing events. Because peptides such as pullulanase often exhibit a range of physiological properties and because such properties may be attributable to different portions of the molecule, a useful pullulanase fragment or pullulanase analog is one which exhibits a biological activity in any biological assay for pullulanase activity. Most preferably the fragment or analog possesses 10%, 40%, 60%, 70%, 80% or at least 90% of the activity of pullulanase (SEQ ID NOS: 2, 4 AND 6), in any in vivo or in vitro pullulanase assay. One method of making such analogs of pullulanase include the synthesis of pullulanase analogs via directed molecular evolution, as discussed infra.

Fragments of pullulanase can be generated by methods known to those skilled in the art. The ability of a candidate fragment to exhibit a biological activity of pullulanase can be assessed by methods known to those skilled in the art as described herein. Also included pullulanase peptides containing residues that are not required for biological activity of the peptide or that result from alternative mRNA splicing or alternative protein processing events.

In order to obtain a pullulanase peptide, pullulanase-encoding DNA can be introduced into an expression vector, the vector introduced into a cell suitable for expression of the desired protein, and the peptide recovered and purified, by prior art methods. Antibodies to the peptides and proteins can be made by immunizing an animal, e.g., a rabbit or mouse, and recovering anti-pullulanase antibodies by prior art methods.

INDUSTRIAL APPLICATIONS OF THE INVENTION

The present invention has many practical applications in industry, as is contemplated herein, this description is intended to be exemplary, and non-inclusive.

In several embodiments, the present invention has contemplated use in ethanol production, baking, fruit juice production, brewing, distilling, winemaking, leather, oils and fats, paper and pulp and the animal feed production.

In other embodiments, the present invention has contemplated use as the active "biological" component of detergents and cleaning products. Here, proteases, amylases and lipases are used to break down protein, starch and fatty stains. Embodiments of the invention include testing the compatibility of enzymes with detergent ingredients by doing stability studies and testing them in a variety of formulations.

In another embodiment, the present invention has contemplated use in the textile industry, mainly in the finishing of fabrics and garments. Major applications include: Desizing, removal of size, (that is, removal of stiff elements of fiber), from threads in fabrics after weaving. Bio-polishing-a process to reduce pilling tendency and to give fabrics a smoother and glossier appearance. Bio-stoning-a process where a small dose of enzyme can replace traditional pumice stones used in stonewashing of denim to achieve a worn look.

In yet another embodiment, the present invention has contemplated enzymatic uses for the liquefaction and saccharification of starch into glucose and isomerisation into fructose. The present invention may be used to convert large volumes of corn and other grains into sweeteners, like high fructose corn syrup and maltose syrup.

EXAMPLES

In the experimental disclosure which follows, the following abbreviations apply: eq (equivalents); M (Molar); μM (micromolar); N (normal); mol (moles); mmol (millimoles); μmol (micromoles); nmol (nanomoles); g (grams); mg (milligrams); kg (kilograms); μg (micrograms); L (liters); ml (milliliters); μl (microliters); cm (centimeters); mm (millimeters); μm (micrometers); nm (nanometers); ° C. (degrees Centigrade); h (hours); min (minutes); sec (seconds); msec (milliseconds); TLC (thin layer chromatography); nt (nucleotides); Q (glutamine); E (glutamic acid); CAP (choloroamphenicol).

The present invention is described in further detain in the following examples which are not in any way intended to limit the scope of the invention as claimed. The attached Figures are meant to be considered as integral parts of the specification and description of the invention. All references cited are herein specifically incorporated by reference for all that is described therein. The following examples are offered to illustrate, but not to limit the claimed invention.

Example 1

Design of Pullulanase Variants

The following pullulanase variants were designed (see, FIG. 1).

"PUL" This is the 'wild-type' *B. deramificans* pullulanase, identical to the molecule expressed by BMP139. The gene has been codon-optimized, is driven by the amyL (LAT) promoter, and has an amyL signal sequence. The differences between this construction and the one present in BMP139 are as follows (see, FIG. 2). First, the new construction has a codon-optimized coding region, as compared to the native coding sequence in BMP139. Second, the new construction has a shorter amyL promoter region of 100 nt, versus approximately 800 nt in BMP139. Third, the new construction has the amyL terminator, while BMP139 has the *B. deramificans* pullulanase terminator. Both the new and the old construction have the amyL signal sequence and express identical pullulanase molecules. While the molecule expressed by this new construction is identical to the current product, there may be a benefit with respect to production titers as a result of the codon optimization. Referring to FIG. 7B, the immature form of the PUL polypeptide is SEQ ID NO: 2, with the signal sequence being SEQ ID NO: 11 and the mature form of the PUL polypeptide being SEQ ID NO: 12.

"PULm104" This is the *B. deramificans* pullulanase from which the N-terminal 104 amino acids have been deleted. The construction encompasses the amyL promoter, amyL signal sequence, codon-optimized pullulanase coding region lacking the sequence encoding the N-terminal 104 amino acids of the mature pullulanase, and the amyL terminator. The truncated pullulanase PULm104 resembles the PULm98 and PULm102 molecules produced upon clipping full-length pullulanase N-terminally at E99 and E103. The pullulanase was deleted up to amino acid 104 in order to obtain an ideal signal peptidase target consensus sequence between the amyL signal sequence and the pullulanase sequence: ASA-A (SEQ ID NO: 17). The rationale behind this truncated pullulanase variant follows previous surprising observations in which a higher specific activity was seen for the clipped pullulanase variants compared to the full-length molecule. Referring to FIG. 8B, the immature form of the PULm104 polypeptide is SEQ ID NO: 4, with the signal sequence being SEQ ID NO: 13 and the mature form of the PULm104 polypeptide being SEQ ID NO: 14.

"PUL_E99Q_E103Q" This is the *B. deramificans* pullulanase in which the protease target motifs at E99 and E103 have been modified into Q99 and Q103, with the objective of making the pullulanase molecule resistant to clipping at E99 and E103. Furthermore, in case post-51 h degradation of pullulanase would be dependent on initial clipping at E99 and E103, this modification would be expected to prevent degradation and activity drop after 51 h. Referring to FIG. 9B, the immature form of the PUL_E99Q_E103Q polypeptide is SEQ ID NO: 6, with the signal sequence being SEQ ID NO: 15 and the mature form of the PUL polypeptide being SEQ ID NO: 16.

Example 2

Construction and Transformation of Plasmids

Two codon-optimized pullulanase constructs were synthesized, one encoding the 'wild-type' pullulanase protein, the other encoding the E99Q_E103Q variant.

Both encompassed 57 nucleotides of amyL promoter (previously demonstrated to allow cloning in *E. coli*; longer promoter stretches are lethal), the amyL signal sequence, the codon-optimized pullulanase (variant) sequence, and the amyL terminator. These constructs served as templates for PCR-construction of the three pullulanase constructions described above:

"PUL" The following primers were used to amplify the 'wild-type' pullulanase construct from the synthetic 'wild-type' pullulanase construct (XhoI site in bold):

Plat5-XhoI_FW:
[SEQ ID NO.: 7]
ccccgctcgaggcttttcttttggaagaaaatagggaaaatggtact tgttaaaaattcggaatatttatacaatatcatatgtttacattgaaagg gg.

Tlat-XhoI_RV:
[SEQ ID NO.: 8]
tggaatctcgaggttttatcctttaccttgtctcc.

2) "PULm104" The expression cassette for the truncated pullulanase was generated by fusion PCR. The following two fragments were amplified from the synthetic 'wild-type' pullulanase construct, and subsequently fused:

A fragment covering the amyL promoter and amyL signal sequence.
A fragment covering the truncated pullulanase coding sequence and the amyL terminator.

Ad A)
The following primers were used for amplification of the amyL promoter and signal sequence:

Plat5-XhoI_FW
[SEQ ID NO.: 7]
(see above).

ssLAT-PULm104_RV:
[SEQ ID NO.: 9]
gcgttgctgactgccggtttagcagctgctgaagctgcagaatgaggcag
c
(fusion primer; reverse pullulanase sequence starting at codon 105 in bold).

Ad B)
The following primers were used for amplification of the pullulanase coding sequence and the amyL terminator:

ssLAT-PULm104_FW:
[SEQ ID NO.: 10]
gctgcctcattctgcagcttcagcagctgctaaaccggcagtcagcaacg
c
(fusion primer; pullulanase sequence starting at codon 105 in bold).

Tlat-XhoI_RV:
[SEQ ID NO.: 8]
(see above).

The fusion primers each encompass two sequence stretches that are 312 nt apart in the template sequence (representing the N-terminal 104 amino acids). The two PCR fragments described under A) and B) were fused in a PCR reaction using primers Plat5-XhoI_FW and Tlat-XhoI_RV.

"PUL_E99Q_E103Q" The construction of the E99Q_E103Q pullulanase variant was identical to that of the 'wild-type' pullulanase construct (see, 1 above), with the E99Q_E103Q synthetic construct as template.

Figure 3:
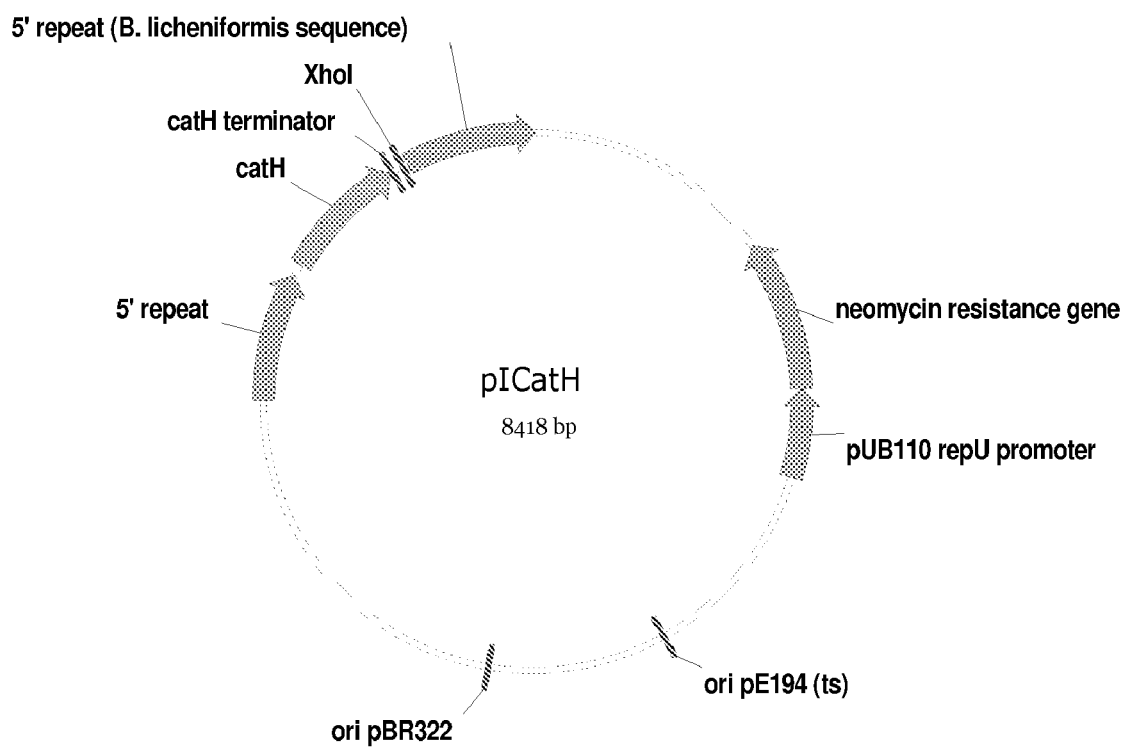
FIG. 3 shows a schematic representation of the pICatH vector. The pICatH vector contains a temperature sensitive origin of replication (ori pE194, for replication in *Bacillus*), ori pBR322 (for amplification in *E. coli*), a neomycin resistance gene for selection, and the native *B. licheniformis* chloramphenicol resistance gene (cat) with repeats for selection, chromosomal integration and cassette amplification.
Figure 5:
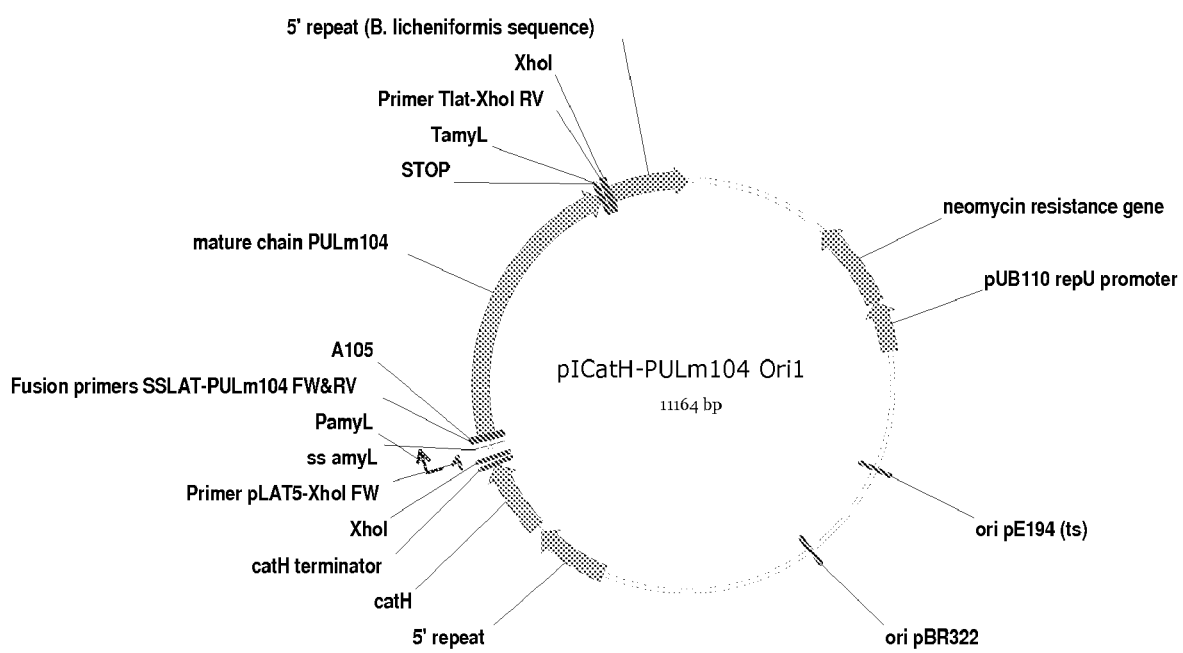
FIG. 5 shows a schematic representation of the pICatH-PULm104Ori1 construct.
Figure 6:
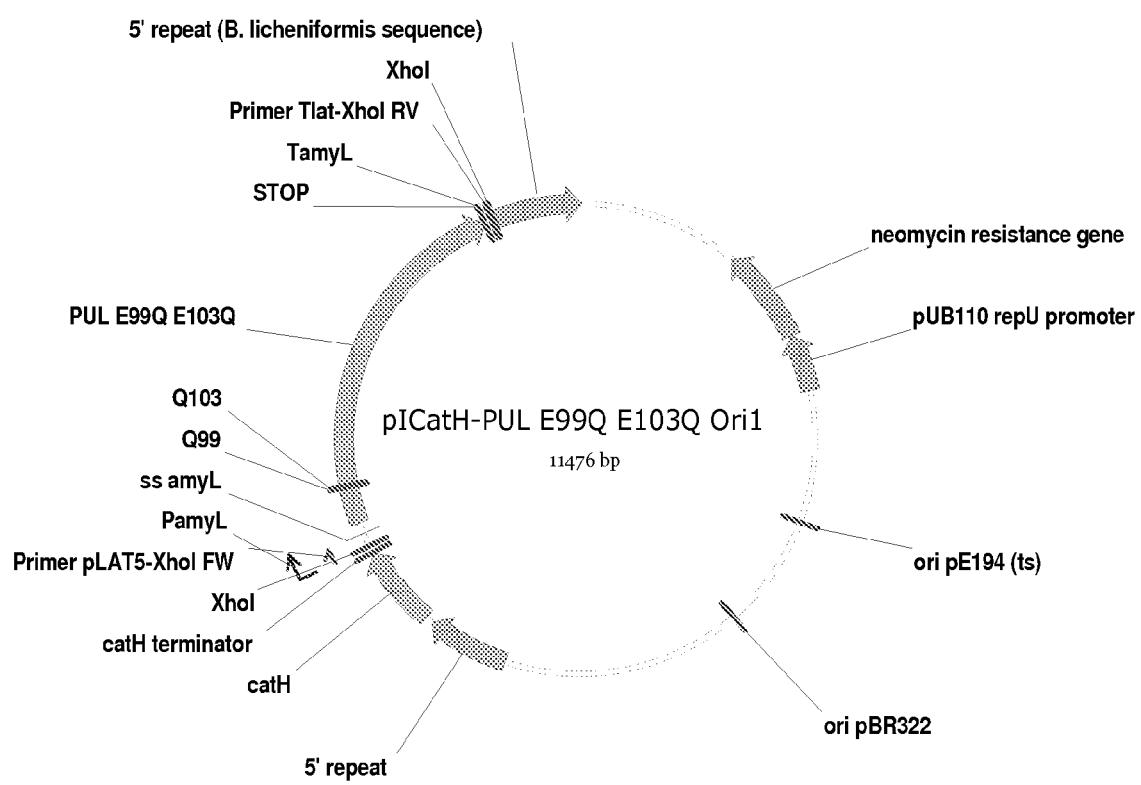
FIG. 6 shows a schematic representation of the pICatH-PUL_E99Q_E103Q Ori construct.

The generated fragments were cloned in two orientations into the XhoI site of the *B. licheniformis* integration vector pICatH (FIG. 3). This resulted in six constructs, pICatH-PUL-Ori1 (FIG. 4), pICatH-PUL-Ori2, pICatH-PULm104-Ori1 (FIG. 5), pICatH-PULm104-Ori2, pICatH-PUL_E99Q_E103Q-Ori1 (FIG. 6), and pICatH-PUL_E99Q_E103Q-Ori2.

Figure 4:
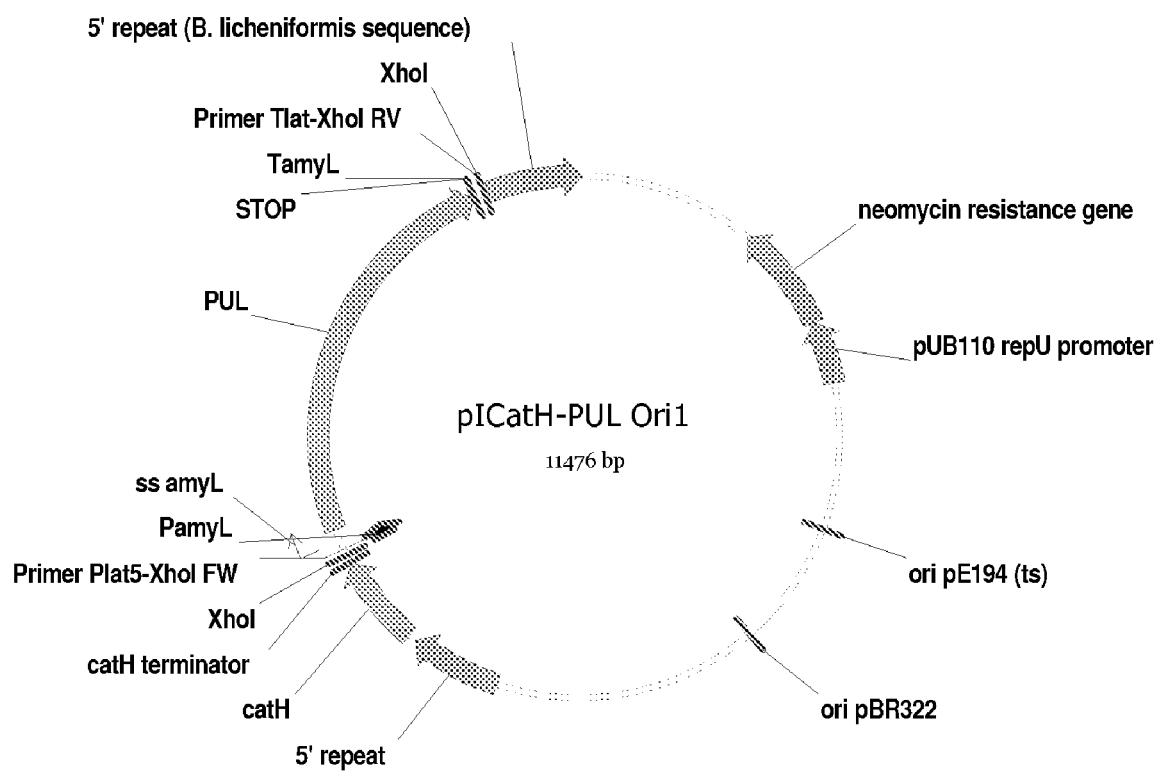
FIG. 4 shows a schematic representation of the pICatH-PUL Ori1 construct.

The Ori1 and Ori2 constructs have opposite orientations of the pullulanase gene relative to the chloramphenicol-resistance (catH) gene, FIGS. 4(*a*), 5(*a*) and 6(*a*) show plasmid maps of the three Ori1 constructs.

All six constructs were transformed into *B. subtilis*, and screened for halo formation in AZCL-pullulan (Megazyme) overlays (0.1% in 100 mM NaAc pH 5, 1% agar). pICatH-PULm104 transformants produced larger halos than transformants of either full-length pullulanase. Constructs were sequence verified and transformed into *B. licheniformis* host strains BML612 and BML780 using protoplast transformation.

Example 3

Integration into the *B. licheniformis* Genome

After transformation, transformants were selected on minimal regeneration plates containing 5 μg/ml chloramphenicol and 10 μg/ml neomycin. Transformants were replica-plated to two Heart Infusion-agar plates (known to those skilled in the art) containing the same antibiotics, one of which was overlaid with AZCL-pullulan to select pullulanase positive transformants. Analogous to the situation in *B. subtilis*, PULm104 transformants showed the largest halos. Plasmids were integrated into the catH locus on the *B. licheniformis* chromosome. Thus, the following set of integrants, as shown in Table 2, was pursued further for excision/amplification:

TABLE 2

| |
| --- |
| BML612 PUL Ori1 |
| BML612 PUL Ori2 |
| BML612 PULm104 Ori1 |
| BML612 PULm104 Ori2 |
| BML612 PUL_E99Q_E103Q Ori1 |
| BML612 PUL_E99Q_E103Q Ori2 |
| BML780 PUL Ori1 |
| BML780 PUL Ori2 |
| BML780 PULm104 Ori1 |
| BML780 PULm104 Ori2 |
| BML780 PUL_E99Q_E103Q Ori1 |
| BML780 PUL_E99Q_E103Q Ori2 |

Plasmid excision and cassette amplification was performed as follows. Strains without foreign DNA ("exempt strains") were obtained through excision of vector sequences ('loop-outs'), leaving only the catH-pullulanase expression cassette integrated in the chromosome. The expression cassette was then amplified by subjecting the strains to a stepwise increase in chloramphenicol concentration (5, 25, 50, 75 μg/ml). Pullulanase production was monitored by overlaying replica plates with AZCL-pullulan after each amplification step. Of each strain, four amplification levels were obtained: CAP5, CAP25, CAP50 and CAP75.

Example 4

Evaluation of *B. licheniformis* Pullulanase Strains

Strains were picked in duplicate at all amplification levels to a single large Heart Infusion-agar plate containing 5 μg/ml chloramphenicol and grown overnight at 37° C. The pullulanase production strain BMP139 was included as benchmark. Pullulanase activity was visualized by overlaying the plate with AZCL-pullulan agar. The overlay was incubated 8 h at 37° C., followed by 16 h incubation at room temperature. The result is summarized in Table 3 below.

TABLE 3

| Strain | CAP5 | CAP25 | CAP50 | CAP75 |
|---|---|---|---|---|
| BML612 PUL Ori1 | + | + | + | ++ |
| BML612 PUL Ori2 | + | + | + | ++ |
| BML612 PULm104 Ori1 | + | ++ | ++ | +++ |
| BML612 PULm104 Ori2 | + | + | +++ | +++ |
| BML612 PUL_E99Q_E103Q Ori1 | + | + | ++ | ++ |
| BML612 PUL_E99Q_E103Q Ori2 | + | + | ++ | ++ |
| BML780 PUL Ori1 | + | + | + | ++ |
| BML780 PUL Ori2 | + | + | ++ | ++ |
| BML780 PULm104 Ori1 | ++ | ++ | +++ | +++++ |
| BML780 PULm104 Ori2 | ++ | ++ | +++ | +++++ |
| BML612 PUL_E99Q_E103Q Ori1 | ++ | ++ | ++ | ++ |
| BML612 PUL_E99Q_E103Q Ori2 | + | ++ | ++ | +++ |
| BMP139 | | | | ++ |

Legend:
+ = halo diameter 7-9 mm
++ = halo diameter 10-12 mm
+++ = halo diameter 13-15 mm
++++ = halo diameter 16-18 mm
+++++ = halo diameter 19-21 mm From the evaluation, it is clear that amplification results in increase in titers and/or performance. More specific conclusions:
1) The N-terminally truncated PUL strains (PULm104) have a very pronounced performance benefit over the full-length pullulanase strains. BML780 PULm104 CAP75 strains produce halos with 2.5 fold-increased surface (over 1.5 times increased diameter) over those of the BMP139 strain and the BML780 PUL CAP75 strains. This suggests that the shorter molecule is produced at higher titers, or its activity is increased compared to the full-length pullulanase molecules.
2) The PUL_E99Q_E103Q variant may have a slight benefit over the 'wild-type' PUL. The halos produced by BML780 PUL_E99Q_E103Q strains are somewhat larger than those of BML780 PUL strains.
3) The BMP139 production strain appears to be equal in performance to the CAP75 amplified "wild-type" PUL strains. Thus, based on plate evaluation, codon-optimization does not result in increased performance.
4) BML780 strains generally have better performance than BML612 strains. This observation is in line with previous data on degradation of pullulanase in the BML612 background. The fact that the BML612 pullulanase strains constructed here still show reasonable AZCL-clearing suggests that on plates, pullulanase is relatively stable even in the BML612 background.
5) No clear performance differences are observed between Ori1 and Ori2 pullulanase strains.

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

We claim:

1. A fusion protein comprising a pullulanase protein having the amino acid sequence of SEQ ID NO: 14 fused in-frame to a signal sequence and a peptidase target sequence, wherein the peptidase target sequence is between the signal sequence and the amino acid sequence of SEQ ID NO: 14.

2. The fusion protein of claim 1, wherein the peptidase target sequence has the amino acid sequence of SEQ ID NO: 17.

3. A truncated pullulanase protein having the amino acid sequence of SEQ ID NO: 14.

4. A variant pullulanase protein having the amino acid sequence of SEQ ID NO: 12.

* * * * *

SEQUENCE LISTING

```
<160> NUMBER OF SEQ ID NOS: 17

<210> SEQ ID NO 1
<211> LENGTH: 2871
<212> TYPE: DNA
<213> ORGANISM: Artificial
<220> FEATURE:
<223> OTHER INFORMATION: synthetic codon opitimized sequence from
      Bacillus deramificans

<400> SEQUENCE: 1
atgaaacaac aaaaacggct ttacgcccga ttgctgacgc tgttatttgc gctcatcttc      60
ttgctgcctc attctgcagc ttcagcagat ggcaatacga cgacgatcat cgtccattat     120
tttagaccgg cgggagatta tcaaccgtgg agcctttgga tgtggccgaa agatggagga     180
ggagcggaat atgattttaa ccagccggca gattcacttg gagcagtcgc ctcagcagat     240
attccgggaa atccgagcca agtcggcatc atcgtcagaa cacaggattg gacgaaagat     300
gtcagcgccg atcgctatat cgatctgagc aaaggcaatg aagtctggct ggtcgaaggc     360
aacagccaga tcttttatag cgaaaaagac gccgaagatg ctgctaaacc ggcagtcagc     420
aacgcttatc tggatgccag caaccaagtc ctggtcaaac tgagccaacc gctgacactt     480
ggagaaggag cgagcggatt tacggtccat gatgacacgg cgaacaaaga tatcccggtc     540
acgagcgtta aagatgctag cctgggccaa gatgtcacag cagttctggc gggcacgttt     600
```

```
caacatatct tggcggatc agattgggca ccggataatc acagcacgct gctgaaaaaa    660
gtcacgaaca acctgtatca gtttagcgga gatctgccgg aaggcaacta tcaatataaa    720
gtcgccctga acgatagctg gaacaatccg agctatccga gcgataacat caatctgaca    780
gtcccggcag gcggagcaca tgtcacgttt agctatatcc cgagcacaca tgccgtctat    840
gacacgatca acaacccgaa cgccgatctt caagtcgaaa gcggcgtcaa acggatctg     900
gtcacagtca cattgggaga agatccggat gtcagccata cactgagcat ccaaacggat    960
ggctatcaag cgaaacaagt catcccgaga acgtcctga acagcagcca gtattattat    1020
agcggcgatg atctgggcaa cacgtataca caaaaagcga cgacgtttaa agtttgggcg    1080
ccgacaagca cacaagtcaa cgtcctgctg tatgattcag caacaggcag cgtcacaaaa    1140
atcgtcccga tgacagcatc aggacatgga gtctgggaag cgacggtcaa ccaaaacctg    1200
gaaaactggt attatatgta tgaagtcacg ggccaaggat caacaagaac agcggtcgat    1260
ccgtatgcta cagcaatcgc cccgaatgga acaagaggca tgatcgtcga tctggcaaaa    1320
acagacccgg caggctggaa tagcgataaa catatcacgc cgaaaaacat cgaagatgaa    1380
gtcatctatg aaatggacgt ccgggatttt agcatcgatc cgaacagcgg catgaaaaac    1440
aaaggcaaat atctggcgct gacggaaaaa ggaacaaaag gcccggataa cgtcaaaaca    1500
ggcatcgata gcctgaaaca actgggcatc acacatgtcc aactgatgcc ggtctttgct    1560
agcaatagcg tcgatgaaac ggacccgaca caagataact ggggctatga cccgagaaat    1620
tatgatgtcc cggaaggcca atatgccacg aacgccaatg aaacgcccg gatcaaagaa    1680
tttaaagaaa tggtcctgag ccttcataga gaacatatcg gcgtcaacat ggacgtcgtc    1740
tataaccata cgtttgccac acagatcagc gactttgata aaatcgtgcc ggaatattat    1800
tatcggacgg atgacgccgg caattatacg aatggcagcg gcacaggaaa tgaaatcgcc    1860
gccgaaagac cgatggtcca gaaatttatc atcgacagcc ttaaaatattg ggtcaacgaa    1920
tatcatatcg acggctttcg ctttgatctg atggcgctgc tgggcaaaga tacaatgagc    1980
aaagcggcga gcgaacttca tgctatcaat ccgggcatcg ctctttatgg agaaccgtgg    2040
acaggaggaa catcagcact gccggatgat caactgctga caaaaggcgc ccaaaaagga    2100
atgggagtcg ccgtctttaa cgacaacctg agaaatgccc tggatggcaa cgttttttgat    2160
agcagcgccc aaggatttgc tacaggagcg acaggactga cagatgccat caaaaatggc    2220
gtcgaaggca gcatcaacga ttttacaagc agcccgggag aaacgatcaa ttatgtcacg    2280
agccatgaca actatacgct gtgggacaaa atcgctctga gcaacccgaa tgatagcgaa    2340
gcggaccgga tcaaaatgga tgaactggca caagcagtcg tcatgacatc acaaggcgtc    2400
ccgtttatgc aaggcggaga agaaatgctg agaacgaaag cggcaacga caacagctat    2460
aatgccggcg atgccgtcaa tgaatttgac tggagccgga agcacaata tccggacgtc    2520
tttaactatt attcaggact tatccatctg agactggacc atccggcgtt tagaatgacg    2580
acggcgaacg aaatcaacag ccatcttcag tttctgaaca gcccggaaaa tacggtcgcc    2640
tatgaactga cggaccatgt gaacaaagac aaatgggca acatcatcgt cgtttataac    2700
ccgaacaaaa cggtcgccac aatcaatctt ccgagcggca atgggcaat caatgccaca    2760
agcggcaaag ttggagaaag cacactggga caagcagaag gatcagtcca agtcccggga    2820
atcagcatga tgatccttca tcaagaagtc agcccggacc acggcaaaaa a            2871
```

<210> SEQ ID NO 2
<211> LENGTH: 957
<212> TYPE: PRT

<213> ORGANISM: Bacillus deramificans

<400> SEQUENCE: 2

```
Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ser Ala Asp Gly Asn
            20                  25                  30

Thr Thr Thr Ile Ile Val His Tyr Phe Arg Pro Ala Gly Asp Tyr Gln
        35                  40                  45

Pro Trp Ser Leu Trp Met Trp Pro Lys Asp Gly Gly Ala Glu Tyr
    50                  55                  60

Asp Phe Asn Gln Pro Ala Asp Ser Leu Gly Ala Val Ala Ser Ala Asp
65                  70                  75                  80

Ile Pro Gly Asn Pro Ser Gln Val Gly Ile Val Arg Thr Gln Asp
                85                  90                  95

Trp Thr Lys Asp Val Ser Ala Asp Arg Tyr Ile Asp Leu Ser Lys Gly
            100                 105                 110

Asn Glu Val Trp Leu Val Glu Gly Asn Ser Gln Ile Phe Tyr Ser Glu
            115                 120                 125

Lys Asp Ala Glu Asp Ala Ala Lys Pro Ala Val Ser Asn Ala Tyr Leu
130                 135                 140

Asp Ala Ser Asn Gln Val Leu Val Lys Leu Ser Gln Pro Leu Thr Leu
145                 150                 155                 160

Gly Glu Gly Ala Ser Gly Phe Thr Val His Asp Asp Thr Ala Asn Lys
                165                 170                 175

Asp Ile Pro Val Thr Ser Val Lys Asp Ala Ser Leu Gly Gln Asp Val
                180                 185                 190

Thr Ala Val Leu Ala Gly Thr Phe Gln His Ile Phe Gly Gly Ser Asp
            195                 200                 205

Trp Ala Pro Asp Asn His Ser Thr Leu Leu Lys Lys Val Thr Asn Asn
210                 215                 220

Leu Tyr Gln Phe Ser Gly Asp Leu Pro Glu Gly Asn Tyr Gln Tyr Lys
225                 230                 235                 240

Val Ala Leu Asn Asp Ser Trp Asn Asn Pro Ser Tyr Pro Ser Asp Asn
                245                 250                 255

Ile Asn Leu Thr Val Pro Ala Gly Gly Ala His Val Thr Phe Ser Tyr
            260                 265                 270

Ile Pro Ser Thr His Ala Val Tyr Asp Thr Ile Asn Asn Pro Asn Ala
        275                 280                 285

Asp Leu Gln Val Glu Ser Gly Val Lys Thr Asp Leu Val Thr Val Thr
290                 295                 300

Leu Gly Glu Asp Pro Asp Val Ser His Thr Leu Ser Ile Gln Thr Asp
305                 310                 315                 320

Gly Tyr Gln Ala Lys Gln Val Ile Pro Arg Asn Val Leu Asn Ser Ser
                325                 330                 335

Gln Tyr Tyr Tyr Ser Gly Asp Asp Leu Gly Asn Thr Tyr Thr Gln Lys
            340                 345                 350

Ala Thr Thr Phe Lys Val Trp Ala Pro Thr Ser Thr Gln Val Asn Val
        355                 360                 365

Leu Leu Tyr Asp Ser Ala Thr Gly Ser Val Thr Lys Ile Val Pro Met
    370                 375                 380

Thr Ala Ser Gly His Gly Val Trp Glu Ala Thr Val Asn Gln Asn Leu
385                 390                 395                 400

Glu Asn Trp Tyr Tyr Met Tyr Glu Val Thr Gly Gln Gly Ser Thr Arg
```

```
                    405                 410                 415
Thr Ala Val Asp Pro Tyr Ala Thr Ala Ile Ala Pro Asn Gly Thr Arg
                420                 425                 430
Gly Met Ile Val Asp Leu Ala Lys Thr Asp Pro Ala Gly Trp Asn Ser
            435                 440                 445
Asp Lys His Ile Thr Pro Lys Asn Ile Glu Asp Val Ile Tyr Glu
        450                 455                 460
Met Asp Val Arg Asp Phe Ser Ile Asp Pro Asn Ser Gly Met Lys Asn
465                 470                 475                 480
Lys Gly Lys Tyr Leu Ala Leu Thr Glu Lys Gly Thr Lys Gly Pro Asp
                485                 490                 495
Asn Val Lys Thr Gly Ile Asp Ser Leu Lys Gln Leu Gly Ile Thr His
            500                 505                 510
Val Gln Leu Met Pro Val Phe Ala Ser Asn Ser Val Asp Glu Thr Asp
        515                 520                 525
Pro Thr Gln Asp Asn Trp Gly Tyr Asp Pro Arg Asn Tyr Asp Val Pro
        530                 535                 540
Glu Gly Gln Tyr Ala Thr Asn Ala Asn Gly Asn Ala Arg Ile Lys Glu
545                 550                 555                 560
Phe Lys Glu Met Val Leu Ser Leu His Arg Glu His Ile Gly Val Asn
                565                 570                 575
Met Asp Val Val Tyr Asn His Thr Phe Ala Thr Gln Ile Ser Asp Phe
            580                 585                 590
Asp Lys Ile Val Pro Glu Tyr Tyr Arg Thr Asp Asp Ala Gly Asn
        595                 600                 605
Tyr Thr Asn Gly Ser Gly Thr Gly Asn Glu Ile Ala Ala Glu Arg Pro
        610                 615                 620
Met Val Gln Lys Phe Ile Ile Asp Ser Leu Lys Tyr Trp Val Asn Glu
625                 630                 635                 640
Tyr His Ile Asp Gly Phe Arg Phe Asp Leu Met Ala Leu Leu Gly Lys
                645                 650                 655
Asp Thr Met Ser Lys Ala Ala Ser Glu Leu His Ala Ile Asn Pro Gly
            660                 665                 670
Ile Ala Leu Tyr Gly Glu Pro Trp Thr Gly Gly Thr Ser Ala Leu Pro
        675                 680                 685
Asp Asp Gln Leu Leu Thr Lys Gly Ala Gln Lys Gly Met Gly Val Ala
        690                 695                 700
Val Phe Asn Asp Asn Leu Arg Asn Ala Leu Asp Gly Asn Val Phe Asp
705                 710                 715                 720
Ser Ser Ala Gln Gly Phe Ala Thr Gly Ala Thr Gly Leu Thr Asp Ala
                725                 730                 735
Ile Lys Asn Gly Val Glu Gly Ser Ile Asn Asp Phe Thr Ser Ser Pro
            740                 745                 750
Gly Glu Thr Ile Asn Tyr Val Thr Ser His Asp Asn Tyr Thr Leu Trp
        755                 760                 765
Asp Lys Ile Ala Leu Ser Asn Pro Asn Asp Ser Glu Ala Asp Arg Ile
        770                 775                 780
Lys Met Asp Glu Leu Ala Gln Ala Val Val Met Thr Ser Gln Gly Val
785                 790                 795                 800
Pro Phe Met Gln Gly Gly Glu Met Leu Arg Thr Lys Gly Gly Asn
        805                 810                 815
Asp Asn Ser Tyr Asn Ala Gly Asp Ala Val Asn Glu Phe Asp Trp Ser
            820                 825                 830
```

```
Arg Lys Ala Gln Tyr Pro Asp Val Phe Asn Tyr Tyr Ser Gly Leu Ile
        835                 840                 845

His Leu Arg Leu Asp His Pro Ala Phe Arg Met Thr Thr Ala Asn Glu
    850                 855                 860

Ile Asn Ser His Leu Gln Phe Leu Asn Ser Pro Glu Asn Thr Val Ala
865                 870                 875                 880

Tyr Glu Leu Thr Asp His Val Asn Lys Asp Lys Trp Gly Asn Ile Ile
                885                 890                 895

Val Val Tyr Asn Pro Asn Lys Thr Val Ala Thr Ile Asn Leu Pro Ser
            900                 905                 910

Gly Lys Trp Ala Ile Asn Ala Thr Ser Gly Lys Val Gly Glu Ser Thr
        915                 920                 925

Leu Gly Gln Ala Glu Gly Ser Val Gln Val Pro Gly Ile Ser Met Met
    930                 935                 940

Ile Leu His Gln Glu Val Ser Pro Asp His Gly Lys Lys
945                 950                 955
```

```
<210> SEQ ID NO 3
<211> LENGTH: 2559
<212> TYPE: DNA
<213> ORGANISM: Artificial
<220> FEATURE:
<223> OTHER INFORMATION: synthetic codon optimized pullulanase

<400> SEQUENCE: 3
atgaaacaac aaaaacggct ttacgcccga ttgctgacgc tgttatttgc gctcatcttc      60
ttgctgcctc attctgcagc ttcagcagct gctaaaccgg cagtcagcaa cgcttatctg     120
gatgccagca ccaagtcct ggtcaaactg agccaaccgc tgacacttgg agaaggagcg      180
agcggattta cggtccatga tgacacgcg aacaaagata tcccggtcac gagcgttaaa      240
gatgctagcc tgggccaaga tgtcacagca gttctggcgg gcacgtttca acatatcttt     300
ggcggatcag attgggcacc ggataatcac agcacgctgc tgaaaaagt cacgaacaac      360 ctgtatcagt ttagcggaga tctgccggaa ggcaactatc aatataaagt cgccctgaac     420
gatagctgga caatccgag ctatccgagc gataacatca atctgacagt cccggcaggc     480
ggagcacatg tcacgtttag ctatatcccg agcacacatg ccgtctatga cacgatcaac     540 aaccccgaacg ccgatcttca gtcgaaagc ggcgtcaaaa cggatctggt cacagtcaca     600
ttgggagaag atccggatgt cagccataca ctgagcatcc aaacggatgg ctatcaagcg     660
aaacaagtca tcccgagaaa cgtcctgaac agcagccagt attattatag cggcgatgat     720
ctgggcaaca cgtatacaca aaaagcgacg acgtttaaag tttgggcgcc gacaagcaca     780
caagtcaact tcctgctgta tgattcagca acaggcagcg tcacaaaaat cgtcccgatg     840
acagcatcag acatggagt ctgggaagcg acggtcaacc aaaacctgga aaactggtat     900
tatatgtatg aagtcacggg ccaaggatca acaagaacag cggtcgatcc gtatgctaca     960
gcaatcgccc cgaatggaac aagaggcatg atcgtcgatc tggcaaaaac agacccggca    1020
ggctggaata gcgataaaca tatcacgccg aaaaacatcg aagatgaagt catctatgaa    1080
atggacgtcc gggattttag catcgatccg aacagcggca tgaaaaacaa aggcaaatat    1140
ctggcgctga cggaaaaagg aacaaaaggc ccgataacg tcaaaacagg catcgatagc    1200
ctgaaacaac tgggcatcac acatgtccaa ctgatgccgg tctttgctag caatagcgtc    1260
gatgaaacgg acccgacaca agataactgg ggctatgacc cgagaaatta tgatgtcccg    1320
gaaggccaat atgccacgaa cgccaatgga acgcccggga tcaaagaatt taagaaaatg    1380
```

```
gtcctgagcc ttcatagaga acatatcggc gtcaacatgg acgtcgtcta taaccatacg    1440
tttgccacac agatcagcga ctttgataaa atcgtgccgg aatattatta tcggacggat    1500
gacgccggca attatacgaa tggcagcggc acaggaaatg aaatcgccgc cgaaagaccg    1560
atggtccaga aatttatcat cgacagcctt aaatattggg tcaacgaata tcatatcgac    1620
ggctttcgct ttgatctgat ggcgctgctg gcaaagata caatgagcaa agcggcgagc    1680
gaacttcatg ctatcaatcc gggcatcgct ctttatggag aaccgtggac aggaggaaca    1740
tcagcactgc cggatgatca actgctgaca aaaggcgccc aaaaaggaat gggagtcgcc    1800
gtctttaacg acaacctgag aaatgccctg gatggcaacg tttttgatag cagcgcccaa    1860
ggatttgcta caggagcgac aggactgaca gatgccatca aaaatggcgt cgaaggcagc    1920
atcaacgatt ttacaagcag cccgggagag acgatcaatt atgtcacgag ccatgacaac    1980
tatacgctgt gggacaaaat cgctctgagc aacccgaatg atagcgaagc ggaccggatc    2040
aaaatggatg aactggcaca agcagtcgtc atgacatcac aaggcgtccc gtttatgcaa    2100
ggcggagaag aaatgctgag aacgaaaggc ggcaacgaca acagctataa tgccggcgat    2160
gccgtcaatg aatttgactg gagccggaaa gcacaatatc cggacgtctt taactattat    2220
tcaggactta tccatctgag actggaccat ccggcgttta gaatgacgac ggcgaacgaa    2280
atcaacagcc atcttcagtt tctgaacagc ccggaaaaata cggtcgccta tgaactgacg    2340
gaccatgtga acaaagacaa atggggcaac atcatcgtcg tttataaccc gaacaaaacg    2400
gtcgccacaa tcaatcttcc gagcggcaaa tgggcaatca atgccacaag cggcaaagtt    2460
ggagaaagca cactgggaca agcagaagga tcagtccaag tcccgggaat cagcatgatg    2520
atccttcatc aagaagtcag cccggaccac ggcaaaaaa                           2559
```

<210> SEQ ID NO 4
<211> LENGTH: 853
<212> TYPE: PRT
<213> ORGANISM: Artificial
<220> FEATURE:
<223> OTHER INFORMATION: synthetic codon optimized pullulanase

<400> SEQUENCE: 4

```
Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ser Ala Ala Ala Lys
                20                  25                  30

Pro Ala Val Ser Asn Ala Tyr Leu Asp Ala Ser Asn Gln Val Leu Val
            35                  40                  45

Lys Leu Ser Gln Pro Leu Thr Leu Gly Glu Gly Ala Ser Gly Phe Thr
        50                  55                  60

Val His Asp Asp Thr Ala Asn Lys Asp Ile Pro Val Thr Ser Val Lys
65                  70                  75                  80

Asp Ala Ser Leu Gly Gln Asp Val Thr Ala Val Leu Ala Gly Thr Phe
                85                  90                  95

Gln His Ile Phe Gly Gly Ser Asp Trp Ala Pro Asp Asn His Ser Thr
            100                 105                 110

Leu Leu Lys Lys Val Thr Asn Asn Leu Tyr Gln Phe Ser Gly Asp Leu
        115                 120                 125

Pro Glu Gly Asn Tyr Gln Tyr Lys Val Ala Leu Asn Asp Ser Trp Asn
    130                 135                 140

Asn Pro Ser Tyr Pro Ser Asp Asn Ile Asn Leu Thr Val Pro Ala Gly
145                 150                 155                 160
```

```
Gly Ala His Val Thr Phe Ser Tyr Ile Pro Ser Thr His Ala Val Tyr
                165                 170                 175

Asp Thr Ile Asn Asn Pro Asn Ala Asp Leu Gln Val Glu Ser Gly Val
            180                 185                 190

Lys Thr Asp Leu Val Thr Val Thr Leu Gly Glu Asp Pro Asp Val Ser
            195                 200                 205

His Thr Leu Ser Ile Gln Thr Asp Gly Tyr Gln Ala Lys Gln Val Ile
            210                 215                 220

Pro Arg Asn Val Leu Asn Ser Ser Gln Tyr Tyr Ser Gly Asp Asp
225                 230                 235                 240

Leu Gly Asn Thr Tyr Thr Gln Lys Ala Thr Thr Phe Lys Val Trp Ala
                245                 250                 255

Pro Thr Ser Thr Gln Val Asn Val Leu Leu Tyr Asp Ser Ala Thr Gly
                260                 265                 270

Ser Val Thr Lys Ile Val Pro Met Thr Ala Ser Gly His Gly Val Trp
            275                 280                 285

Glu Ala Thr Val Asn Gln Asn Leu Glu Asn Trp Tyr Tyr Met Tyr Glu
                290                 295                 300

Val Thr Gly Gln Gly Ser Thr Arg Thr Ala Val Asp Pro Tyr Ala Thr
305                 310                 315                 320

Ala Ile Ala Pro Asn Gly Thr Arg Gly Met Ile Val Asp Leu Ala Lys
                325                 330                 335

Thr Asp Pro Ala Gly Trp Asn Ser Asp Lys His Ile Thr Pro Lys Asn
                340                 345                 350

Ile Glu Asp Glu Val Ile Tyr Glu Met Asp Val Arg Asp Phe Ser Ile
            355                 360                 365

Asp Pro Asn Ser Gly Met Lys Asn Lys Gly Lys Tyr Leu Ala Leu Thr
            370                 375                 380

Glu Lys Gly Thr Lys Gly Pro Asp Asn Val Lys Thr Gly Ile Asp Ser
385                 390                 395                 400

Leu Lys Gln Leu Gly Ile Thr His Val Gln Leu Met Pro Val Phe Ala
                405                 410                 415

Ser Asn Ser Val Asp Glu Thr Asp Pro Thr Gln Asp Asn Trp Gly Tyr
            420                 425                 430

Asp Pro Arg Asn Tyr Asp Val Pro Glu Gly Gln Tyr Ala Thr Asn Ala
            435                 440                 445

Asn Gly Asn Ala Arg Ile Lys Glu Phe Lys Glu Met Val Leu Ser Leu
            450                 455                 460

His Arg Glu His Ile Gly Val Asn Met Asp Val Val Tyr Asn His Thr
465                 470                 475                 480

Phe Ala Thr Gln Ile Ser Asp Phe Asp Lys Ile Val Pro Glu Tyr Tyr
                485                 490                 495

Tyr Arg Thr Asp Asp Ala Gly Asn Tyr Thr Asn Gly Ser Gly Thr Gly
            500                 505                 510

Asn Glu Ile Ala Ala Glu Arg Pro Met Val Gln Lys Phe Ile Ile Asp
            515                 520                 525

Ser Leu Lys Tyr Trp Val Asn Gly Tyr His Ile Asp Gly Phe Arg Phe
530                 535                 540

Asp Leu Met Ala Leu Leu Gly Lys Asp Thr Met Ser Lys Ala Ala Ser
545                 550                 555                 560

Glu Leu His Ala Ile Asn Pro Gly Ile Ala Leu Tyr Gly Glu Pro Trp
                565                 570                 575

Thr Gly Gly Thr Ser Ala Leu Pro Asp Asp Gln Leu Leu Thr Lys Gly
            580                 585                 590
```

```
Ala Gln Lys Gly Met Gly Val Ala Val Phe Asn Asp Asn Leu Arg Asn
        595                 600                 605

Ala Leu Asp Gly Asn Val Phe Asp Ser Ser Ala Gln Gly Phe Ala Thr
        610                 615                 620

Gly Ala Thr Gly Leu Thr Asp Ala Ile Lys Asn Gly Val Glu Gly Ser
625                 630                 635                 640

Ile Asn Asp Phe Thr Ser Ser Pro Gly Glu Thr Ile Asn Tyr Val Thr
                645                 650                 655

Ser His Asp Asn Tyr Thr Leu Trp Asp Lys Ile Ala Leu Ser Asn Pro
            660                 665                 670

Asn Asp Ser Glu Ala Asp Arg Ile Lys Met Asp Glu Leu Ala Gln Ala
        675                 680                 685

Val Val Met Thr Ser Gln Gly Val Pro Phe Met Gln Gly Gly Glu Glu
        690                 695                 700

Met Leu Arg Thr Lys Gly Gly Asn Asp Asn Ser Tyr Asn Ala Gly Asp
705                 710                 715                 720

Ala Val Asn Glu Phe Asp Trp Ser Arg Lys Ala Gln Tyr Pro Asp Val
                725                 730                 735

Phe Asn Tyr Tyr Ser Gly Leu Ile His Leu Arg Leu Asp His Pro Ala
            740                 745                 750

Phe Arg Met Thr Thr Ala Asn Glu Ile Asn Ser His Leu Gln Phe Leu
        755                 760                 765

Asn Ser Pro Glu Asn Thr Val Ala Tyr Glu Leu Thr Asp His Val Asn
        770                 775                 780

Lys Asp Lys Trp Gly Asn Ile Ile Val Val Tyr Asn Pro Asn Lys Thr
785                 790                 795                 800

Val Ala Thr Ile Asn Leu Pro Ser Gly Lys Trp Ala Ile Asn Ala Thr
                805                 810                 815

Ser Gly Lys Val Gly Glu Ser Thr Leu Gly Gln Ala Glu Gly Ser Val
            820                 825                 830

Gln Val Pro Gly Ile Ser Met Met Ile Leu His Gln Glu Val Ser Pro
        835                 840                 845

Asp His Gly Lys Lys
    850

<210> SEQ ID NO 5
<211> LENGTH: 2871
<212> TYPE: DNA
<213> ORGANISM: Artificial
<220> FEATURE:
<223> OTHER INFORMATION: synthetic modified pullulanase

<400> SEQUENCE: 5
atgaaacaac aaaaacggct ttacgcccga ttgctgacgc tgttatttgc gctcatcttc      60
ttgctgcctc attctgcagc ttcagcagat ggcaatacga cgacgatcat cgtcccattat    120 tttagaccgg cgggagatta tcaaccgtgg agcctttgga tgtggccgaa agatggagga    180
ggagcggaat atgattttaa ccagccggca gattcacttg agcagtcgc ctcagcagat     240 attccgggaa atccgagcca agtcggcatc atcgtcagaa cacaggattg gacgaaagat    300
gtcagcgccg atcgctatat cgatctgagc aaaggcaatg aagtctggct ggtcgaaggc    360
aacagccaga tctttttatag cgaaaaagac gccgaagatg ctgctaaacc ggcagtcagc    420
aacgcttatc tggatgccag caaccaagtc ctggtcaaac tgagccaacc gctgacactt    480
ggagaaggag cgagcggatt tacggtccat gatgacacgg cgaacaaaga tatcccggtc    540
```

```
acgagcgtta aagatgctag cctgggccaa gatgtcacag cagttctggc gggcacgttt     600
caacatatct ttggcggatc agattgggca ccgataatc acagcacgct gctgaaaaaa      660
gtcacgaaca acctgtatca gtttagcgga gatctgccgg aaggcaacta tcaatataaa    720
gtcgccctga cgatagctg gaacaatccg agctatccga gcgataacat caatctgaca    780
gtcccggcag gcggagcaca tgtcacgttt agctatatcc cgagcacaca tgccgtctat   840
gacacgatca acaacccgaa cgccgatctt caagtcgaaa gcggcgtcaa aacgatctg     900 gtcacagtca cattgggaga agatccggat gtcagccata cactgagcat ccaaacggat    960
ggctatcaag cgaaacaagt catcccgaga aacgtcctga acagcagcca gtattattat   1020
agcggcgatg atctgggcaa cacgtataca caaaaagcga cgacgtttaa agtttgggcg   1080
ccgacaagca cacaagtcaa cgtcctgctg tatgattcag caacaggcag cgtcacaaaa   1140
atcgtcccga tgacagcatc aggacatgga gtctgggaag cgacggtcaa ccaaaacctg   1200
gaaaactggt attatatgta tgaagtcacg ggccaaggat caacaagaac agcggtcgat    1260
ccgtatgcta cagcaatcgc cccgaatgga acaagaggca tgatcgtcga tctggcaaaa    1320
acagacccgg caggctggaa tagcgataaa catatcacgc cgaaaaacat cgaagatgaa    1380
gtcatctatg aaatggacgt ccgggatttt agcatcgatc cgaacagcgg catgaaaaac   1440
aaaggcaaat atctggcgct gacggaaaaa ggaacaaaag gcccggataa cgtcaaaaca   1500
ggcatcgata gcctgaaaca actgggcatc acacatgtcc aactgatgcc ggtctttgct   1560
agcaatagcg tcgatgaaac ggaccccgaca caagataact ggggctatga cccgagaaat    1620
tatgatgtcc cggaaggcca atatgccacg aacgccaatg gaaacgcccg gatcaaagaa    1680
tttaaagaaa tggtcctgag ccttcataga gaacatatcg gcgtcaacat ggacgtcgtc    1740
tataaccata cgttttgccac acagatcagc gactttgata aaatcgtgcc ggaatattat   1800
tatcggacgg atgacgccgg caattatacg aatggcagcg gcacaggaaa tgaaatcgcc    1860
gccgaaagac cgatggtcca gaaatttatc atcgacagcc ttaaatattg ggtcaacgaa    1920
tatcatatcg acggctttcg cttttgatctg atggcgctgc tgggcaaaga tacaatgagc    1980
aaagcggcga gcgaacttca tgctatcaat ccgggcatcc ctctttatgg agaaccgtgg    2040
acaggaggaa catcagcact gccggatgat caactgctga caaaaggcgc ccaaaaagga    2100
atgggagtcg ccgtctttaa cgacaacctg agaaatgccc tggatggcaa cgttttttgat    2160 agcagcgccc aaggatttgc tacaggagcg acaggactga cagatgccat caaaaatggc    2220
gtcgaaggca gcatcaacga ttttacaagc agcccgggag aaacgatcaa ttatgtcacg    2280
agccatgaca actatacgct gtgggacaaa atcgctctga gcaacccgaa tgatagcgaa    2340
gcggaccgga tcaaaatgga tgaactggca caagcagtcg tcatgacatc acaaggcgtc    2400
ccgtttatgc aaggcggaga agaaatgctg agaacgaaag gcggcaacga caacagctat    2460
aatgccggcg atgccgtcaa tgaatttgac tggagccgga aagcacaata tccggacgtc    2520
tttaactatt attcaggact tatccatctg agactggacc atccggcgtt tagaatgacg    2580
acggcgaacg aaatcaacag ccatcttcag tttctgaaca gcccgaaaaa tacggtcgcc    2640
tatgaactga cggaccatgt gaacaaagac aaatgggcaa catcatcgt cgtttataac    2700 ccgaacaaaa cggtcgccac aatcaatctt ccgagcggca atgggcaat caatgccaca    2760 agcggcaaag ttggagaaag cacactggga caagcagaag gatcagtcca agtcccggga    2820
atcagcatga tgatccttca tcaagaagtc agcccggacc acggcaaaaa a            2871
```

<210> SEQ ID NO 6

<211> LENGTH: 957
<212> TYPE: PRT
<213> ORGANISM: Artificial
<220> FEATURE:
<223> OTHER INFORMATION: synthetic modified pullulanase

<400> SEQUENCE: 6

```
Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ser Ala Asp Gly Asn
            20                  25                  30

Thr Thr Thr Ile Ile Val His Tyr Phe Arg Pro Ala Gly Asp Tyr Gln
        35                  40                  45

Pro Trp Ser Leu Trp Met Trp Pro Lys Asp Gly Gly Ala Glu Tyr
    50                  55                  60

Asp Phe Asn Gln Pro Ala Asp Ser Leu Gly Ala Val Ala Ser Ala Asp
65                  70                  75                  80

Ile Pro Gly Asn Pro Ser Gln Val Gly Ile Val Arg Thr Gln Asp
                85                  90                  95

Trp Thr Lys Asp Val Ser Ala Asp Arg Tyr Ile Asp Leu Ser Lys Gly
            100                 105                 110

Asn Glu Val Trp Leu Val Glu Gly Asn Ser Gln Ile Phe Tyr Ser Gln
        115                 120                 125

Lys Asp Ala Gln Asp Ala Ala Lys Pro Ala Val Ser Asn Ala Tyr Leu
    130                 135                 140

Asp Ala Ser Asn Gln Val Leu Val Lys Leu Ser Gln Pro Leu Thr Leu
145                 150                 155                 160

Gly Glu Gly Ala Ser Gly Phe Thr Val His Asp Asp Thr Ala Asn Lys
                165                 170                 175

Asp Ile Pro Val Thr Ser Val Lys Asp Ala Ser Leu Gly Gln Asp Val
            180                 185                 190

Thr Ala Val Leu Ala Gly Thr Phe Gln His Ile Phe Gly Gly Ser Asp
        195                 200                 205

Trp Ala Pro Asp Asn His Ser Thr Leu Leu Lys Lys Val Thr Asn Asn
    210                 215                 220

Leu Tyr Gln Phe Ser Gly Asp Leu Pro Glu Gly Asn Tyr Gln Tyr Lys
225                 230                 235                 240

Val Ala Leu Asn Asp Ser Trp Asn Asn Pro Ser Tyr Pro Ser Asp Asn
                245                 250                 255

Ile Asn Leu Thr Val Pro Ala Gly Gly Ala His Val Thr Phe Ser Tyr
            260                 265                 270

Ile Pro Ser Thr His Ala Val Tyr Asp Thr Ile Asn Asn Pro Asn Ala
        275                 280                 285

Asp Leu Gln Val Glu Ser Gly Val Lys Thr Asp Leu Val Thr Val Thr
    290                 295                 300

Leu Gly Glu Asp Pro Asp Val Ser His Thr Leu Ser Ile Gln Thr Asp
305                 310                 315                 320

Gly Tyr Gln Ala Lys Gln Val Ile Pro Arg Asn Val Leu Asn Ser Ser
                325                 330                 335

Gln Tyr Tyr Tyr Ser Gly Asp Asp Leu Gly Asn Thr Tyr Thr Gln Lys
            340                 345                 350

Ala Thr Thr Phe Lys Val Trp Ala Pro Thr Ser Thr Gln Val Asn Val
        355                 360                 365

Leu Leu Tyr Asp Ser Ala Thr Gly Ser Val Thr Lys Ile Val Pro Met
    370                 375                 380
```

```
Thr Ala Ser Gly His Gly Val Trp Glu Ala Thr Val Asn Gln Asn Leu
385                 390                 395                 400

Glu Asn Trp Tyr Tyr Met Tyr Glu Val Thr Gly Gln Gly Ser Thr Arg
            405                 410                 415

Thr Ala Val Asp Pro Tyr Ala Thr Ala Ile Ala Pro Asn Gly Thr Arg
        420                 425                 430

Gly Met Ile Val Asp Leu Ala Lys Thr Asp Pro Ala Gly Trp Asn Ser
    435                 440                 445

Asp Lys His Ile Thr Pro Lys Asn Ile Glu Asp Glu Val Ile Tyr Glu
    450                 455                 460

Met Asp Val Arg Asp Phe Ser Ile Asp Pro Asn Ser Gly Met Lys Asn
465                 470                 475                 480

Lys Gly Lys Tyr Leu Ala Leu Thr Glu Lys Gly Thr Lys Gly Pro Asp
            485                 490                 495

Asn Val Lys Thr Gly Ile Asp Ser Leu Lys Gln Leu Gly Ile Thr His
            500                 505                 510

Val Gln Leu Met Pro Val Phe Ala Ser Asn Ser Val Asp Glu Thr Asp
        515                 520                 525

Pro Thr Gln Asp Asn Trp Gly Tyr Asp Pro Arg Asn Tyr Asp Val Pro
530                 535                 540

Glu Gly Gln Tyr Ala Thr Asn Ala Asn Gly Asn Ala Arg Ile Lys Glu
545                 550                 555                 560

Phe Lys Glu Met Val Leu Ser Leu His Arg Glu His Ile Gly Val Asn
            565                 570                 575

Met Asp Val Val Tyr Asn His Thr Phe Ala Thr Gln Ile Ser Asp Phe
        580                 585                 590

Asp Lys Ile Val Pro Glu Tyr Tyr Arg Thr Asp Asp Ala Gly Asn
    595                 600                 605

Tyr Thr Asn Gly Ser Gly Thr Gly Asn Glu Ile Ala Ala Glu Arg Pro
    610                 615                 620

Met Val Gln Lys Phe Ile Ile Asp Ser Leu Lys Tyr Trp Val Asn Glu
625                 630                 635                 640

Tyr His Ile Asp Gly Phe Arg Phe Asp Leu Met Ala Leu Leu Gly Lys
            645                 650                 655

Asp Thr Met Ser Lys Ala Ala Ser Glu Leu His Ala Ile Asn Pro Gly
            660                 665                 670

Ile Ala Leu Tyr Gly Glu Pro Trp Thr Gly Gly Thr Ser Ala Leu Pro
        675                 680                 685

Asp Asp Gln Leu Leu Thr Lys Gly Ala Gln Lys Gly Met Gly Val Ala
    690                 695                 700

Val Phe Asn Asp Asn Leu Arg Asn Ala Leu Asp Gly Asn Val Phe Asp
705                 710                 715                 720

Ser Ser Ala Gln Gly Phe Ala Thr Gly Ala Thr Gly Leu Thr Asp Ala
            725                 730                 735

Ile Lys Asn Gly Val Glu Gly Ser Ile Asn Asp Phe Thr Ser Ser Pro
            740                 745                 750

Gly Glu Thr Ile Asn Tyr Val Thr Ser His Asp Asn Tyr Thr Leu Trp
        755                 760                 765

Asp Lys Ile Ala Leu Ser Asn Pro Asn Asp Ser Glu Ala Asp Arg Ile
    770                 775                 780

Lys Met Asp Glu Leu Ala Gln Ala Val Val Met Thr Ser Gln Gly Val
785                 790                 795                 800

Pro Phe Met Gln Gly Gly Glu Glu Met Leu Arg Thr Lys Gly Gly Asn
            805                 810                 815
```

Asp Asn Ser Tyr Asn Ala Gly Asp Ala Val Asn Glu Phe Asp Trp Ser
            820                 825                 830
Arg Lys Ala Gln Tyr Pro Asp Val Phe Asn Tyr Tyr Ser Gly Leu Ile
        835                 840                 845
His Leu Arg Leu Asp His Pro Ala Phe Arg Met Thr Thr Ala Asn Glu
    850                 855                 860
Ile Asn Ser His Leu Gln Phe Leu Asn Ser Pro Glu Asn Thr Val Ala
865                 870                 875                 880
Tyr Glu Leu Thr Asp His Val Asn Lys Asp Lys Trp Gly Asn Ile Ile
                885                 890                 895
Val Val Tyr Asn Pro Asn Lys Thr Val Ala Thr Ile Asn Leu Pro Ser
            900                 905                 910
Gly Lys Trp Ala Ile Asn Ala Thr Ser Gly Lys Val Gly Glu Ser Thr
        915                 920                 925
Leu Gly Gln Ala Glu Gly Ser Val Gln Val Pro Gly Ile Ser Met Met
    930                 935                 940
Ile Leu His Gln Glu Val Ser Pro Asp His Gly Lys Lys
945                 950                 955

<210> SEQ ID NO 7
<211> LENGTH: 102
<212> TYPE: DNA
<213> ORGANISM: Artificial
<220> FEATURE:
<223> OTHER INFORMATION: primer

<400> SEQUENCE: 7
cccccgctcg aggctttcct tttggaagaa aatataggga aaatggtact tgttaaaaat    60
tcggaatatt tatacaatat catatgttta cattgaaagg gg                      102

<210> SEQ ID NO 8
<211> LENGTH: 35
<212> TYPE: DNA
<213> ORGANISM: Artificial
<220> FEATURE:
<223> OTHER INFORMATION: primer

<400> SEQUENCE: 8
tggaatctcg aggtttttatc ctttaccttg tctcc                              35

<210> SEQ ID NO 9
<211> LENGTH: 51
<212> TYPE: DNA
<213> ORGANISM: Artificial
<220> FEATURE:
<223> OTHER INFORMATION: primer

<400> SEQUENCE: 9
gcgttgctga ctgccggttt agcagctgct gaagctgcag aatgaggcag c              51

<210> SEQ ID NO 10
<211> LENGTH: 51
<212> TYPE: DNA
<213> ORGANISM: Artificial
<220> FEATURE:
<223> OTHER INFORMATION: primer

<400> SEQUENCE: 10
gctgcctcat tctgcagctt cagcagctgc taaaccggca gtcagcaacg c              51

<210> SEQ ID NO 11

```
<211> LENGTH: 29
<212> TYPE: PRT
<213> ORGANISM: Bacillus deramificans

<400> SEQUENCE: 11

Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ser Ala
            20                  25

<210> SEQ ID NO 12
<211> LENGTH: 928
<212> TYPE: PRT
<213> ORGANISM: Bacillus deramificans

<400> SEQUENCE: 12

Asp Gly Asn Thr Thr Thr Ile Ile Val His Tyr Phe Arg Pro Ala Gly
1               5                   10                  15

Asp Tyr Gln Pro Trp Ser Leu Trp Met Trp Pro Lys Asp Gly Gly Gly
            20                  25                  30

Ala Glu Tyr Asp Phe Asn Gln Pro Ala Asp Ser Leu Gly Ala Val Ala
        35                  40                  45

Ser Ala Asp Ile Pro Gly Asn Pro Ser Gln Val Gly Ile Ile Val Arg
50                  55                  60

Thr Gln Asp Trp Thr Lys Asp Val Ser Ala Asp Arg Tyr Ile Asp Leu
65                  70                  75                  80

Ser Lys Gly Asn Glu Val Trp Leu Val Glu Gly Asn Ser Gln Ile Phe
                85                  90                  95

Tyr Ser Glu Lys Asp Ala Glu Asp Ala Ala Lys Pro Ala Val Ser Asn
            100                 105                 110

Ala Tyr Leu Asp Ala Ser Asn Gln Val Leu Val Lys Leu Ser Gln Pro
        115                 120                 125

Leu Thr Leu Gly Glu Gly Ala Ser Gly Phe Thr Val His Asp Asp Thr
130                 135                 140

Ala Asn Lys Asp Ile Pro Val Thr Ser Val Lys Asp Ala Ser Leu Gly
145                 150                 155                 160

Gln Asp Val Thr Ala Val Leu Ala Gly Thr Phe Gln His Ile Phe Gly
                165                 170                 175

Gly Ser Asp Trp Ala Pro Asp Asn His Ser Thr Leu Leu Lys Lys Val
            180                 185                 190

Thr Asn Asn Leu Tyr Gln Phe Ser Gly Asp Leu Pro Glu Gly Asn Tyr
        195                 200                 205

Gln Tyr Lys Val Ala Leu Asn Asp Ser Trp Asn Asn Pro Ser Tyr Pro
210                 215                 220

Ser Asp Asn Ile Asn Leu Thr Val Pro Ala Gly Gly Ala His Val Thr
225                 230                 235                 240

Phe Ser Tyr Ile Pro Ser Thr His Ala Val Tyr Asp Thr Ile Asn Asn
                245                 250                 255

Pro Asn Ala Asp Leu Gln Val Glu Ser Gly Val Lys Thr Asp Leu Val
            260                 265                 270

Thr Val Thr Leu Gly Glu Asp Pro Asp Val Ser His Thr Leu Ser Ile
        275                 280                 285

Gln Thr Asp Gly Tyr Gln Ala Lys Gln Val Ile Pro Arg Asn Val Leu
290                 295                 300

Asn Ser Ser Gln Tyr Tyr Tyr Ser Gly Asp Asp Leu Gly Asn Thr Tyr
305                 310                 315                 320
```

```
Thr Gln Lys Ala Thr Thr Phe Lys Val Trp Ala Pro Thr Ser Thr Gln
            325                 330                 335

Val Asn Val Leu Leu Tyr Asp Ser Ala Thr Gly Ser Val Thr Lys Ile
            340                 345                 350

Val Pro Met Thr Ala Ser Gly His Gly Val Trp Glu Ala Thr Val Asn
            355                 360                 365

Gln Asn Leu Glu Asn Trp Tyr Tyr Met Tyr Glu Val Thr Gly Gln Gly
            370                 375                 380

Ser Thr Arg Thr Ala Val Asp Pro Tyr Ala Thr Ala Ile Ala Pro Asn
385                 390                 395                 400

Gly Thr Arg Gly Met Ile Val Asp Leu Ala Lys Thr Asp Pro Ala Gly
            405                 410                 415

Trp Asn Ser Asp Lys His Ile Thr Pro Lys Asn Ile Glu Asp Glu Val
            420                 425                 430

Ile Tyr Glu Met Asp Val Arg Asp Phe Ser Ile Asp Pro Asn Ser Gly
            435                 440                 445

Met Lys Asn Lys Gly Lys Tyr Leu Ala Leu Thr Glu Lys Gly Thr Lys
            450                 455                 460

Gly Pro Asp Asn Val Lys Thr Gly Ile Asp Ser Leu Lys Gln Leu Gly
465                 470                 475                 480

Ile Thr His Val Gln Leu Met Pro Val Phe Ala Ser Asn Ser Val Asp
            485                 490                 495

Glu Thr Asp Pro Thr Gln Asp Asn Trp Gly Tyr Asp Pro Arg Asn Tyr
            500                 505                 510

Asp Val Pro Glu Gly Gln Tyr Ala Thr Asn Ala Asn Gly Asn Ala Arg
            515                 520                 525

Ile Lys Glu Phe Lys Glu Met Val Leu Ser Leu His Arg Glu His Ile
            530                 535                 540

Gly Val Asn Met Asp Val Val Tyr Asn His Thr Phe Ala Thr Gln Ile
545                 550                 555                 560

Ser Asp Phe Asp Lys Ile Val Pro Glu Tyr Tyr Arg Thr Asp Asp
            565                 570                 575

Ala Gly Asn Tyr Thr Asn Gly Ser Gly Thr Gly Asn Glu Ile Ala Ala
            580                 585                 590

Glu Arg Pro Met Val Gln Lys Phe Ile Ile Asp Ser Leu Lys Tyr Trp
            595                 600                 605

Val Asn Glu Tyr His Ile Asp Gly Phe Arg Phe Asp Leu Met Ala Leu
            610                 615                 620

Leu Gly Lys Asp Thr Met Ser Lys Ala Ala Ser Glu Leu His Ala Ile
625                 630                 635                 640

Asn Pro Gly Ile Ala Leu Tyr Gly Glu Pro Trp Thr Gly Gly Thr Ser
            645                 650                 655

Ala Leu Pro Asp Asp Gln Leu Leu Thr Lys Gly Ala Gln Lys Gly Met
            660                 665                 670

Gly Val Ala Val Phe Asn Asp Asn Leu Arg Asn Ala Leu Asp Gly Asn
            675                 680                 685

Val Phe Asp Ser Ser Ala Gln Gly Phe Ala Thr Gly Ala Thr Gly Leu
            690                 695                 700

Thr Asp Ala Ile Lys Asn Gly Val Glu Gly Ser Ile Asn Asp Phe Thr
705                 710                 715                 720

Ser Ser Pro Gly Glu Thr Ile Asn Tyr Val Thr Ser His Asp Asn Tyr
            725                 730                 735

Thr Leu Trp Asp Lys Ile Ala Leu Ser Asn Pro Asn Asp Ser Glu Ala
            740                 745                 750
```

Asp Arg Ile Lys Met Asp Glu Leu Ala Gln Ala Val Val Met Thr Ser
            755                 760                 765
Gln Gly Val Pro Phe Met Gln Gly Gly Glu Met Leu Arg Thr Lys
        770                 775                 780
Gly Gly Asn Asp Asn Ser Tyr Asn Ala Gly Asp Ala Val Asn Glu Phe
785                 790                 795                 800
Asp Trp Ser Arg Lys Ala Gln Tyr Pro Asp Val Phe Asn Tyr Tyr Ser
                805                 810                 815
Gly Leu Ile His Leu Arg Leu Asp His Pro Ala Phe Arg Met Thr Thr
            820                 825                 830
Ala Asn Glu Ile Asn Ser His Leu Gln Phe Leu Asn Ser Pro Glu Asn
            835                 840                 845
Thr Val Ala Tyr Glu Leu Thr Asp His Val Asn Lys Asp Lys Trp Gly
        850                 855                 860
Asn Ile Ile Val Val Tyr Asn Pro Asn Lys Thr Val Ala Thr Ile Asn
865                 870                 875                 880
Leu Pro Ser Gly Lys Trp Ala Ile Asn Ala Thr Ser Gly Lys Val Gly
                885                 890                 895
Glu Ser Thr Leu Gly Gln Ala Glu Gly Ser Val Gln Val Pro Gly Ile
            900                 905                 910
Ser Met Met Ile Leu His Gln Val Ser Pro Asp His Gly Lys Lys
        915                 920                 925

<210> SEQ ID NO 13
<211> LENGTH: 29
<212> TYPE: PRT
<213> ORGANISM: Artificial
<220> FEATURE:
<223> OTHER INFORMATION: synthetic codon optimized pullulanase signal
      peptide

<400> SEQUENCE: 13

Met Lys Gln Gln Lys Arg Leu Tyr Ala Arg Leu Leu Thr Leu Leu Phe
1               5                   10                  15
Ala Leu Ile Phe Leu Leu Pro His Ser Ala Ala Ser Ala
            20                  25

<210> SEQ ID NO 14
<211> LENGTH: 824
<212> TYPE: PRT
<213> ORGANISM: Artificial
<220> FEATURE:
<223> OTHER INFORMATION: synthetic codon optimized pullulanase

<400> SEQUENCE: 14

Ala Ala Lys Pro Ala Val Ser Asn Ala Tyr Leu Asp Ala Ser Asn Gln
1               5                   10                  15
Val Leu Val Lys Leu Ser Gln Pro Leu Thr Leu Gly Glu Gly Ala Ser
            20                  25                  30
Gly Phe Thr Val His Asp Asp Thr Ala Asn Lys Asp Ile Pro Val Thr
        35                  40                  45
Ser Val Lys Asp Ala Ser Leu Gly Gln Asp Val Thr Ala Val Leu Ala
    50                  55                  60
Gly Thr Phe Gln His Ile Phe Gly Gly Ser Asp Trp Ala Pro Asp Asn
65                  70                  75                  80
His Ser Thr Leu Leu Lys Lys Val Thr Asn Asn Leu Tyr Gln Phe Ser
                85                  90                  95
Gly Asp Leu Pro Glu Gly Asn Tyr Gln Tyr Lys Val Ala Leu Asn Asp

-continued

```
                    100                 105                 110
Ser Trp Asn Asn Pro Ser Tyr Pro Ser Asp Asn Ile Asn Leu Thr Val
            115                 120                 125
Pro Ala Gly Gly Ala His Val Thr Phe Ser Tyr Ile Pro Ser Thr His
        130                 135                 140
Ala Val Tyr Asp Thr Ile Asn Asn Pro Asn Ala Asp Leu Gln Val Glu
145                 150                 155                 160
Ser Gly Val Lys Thr Asp Leu Val Thr Val Thr Leu Gly Glu Asp Pro
                165                 170                 175
Asp Val Ser His Thr Leu Ser Ile Gln Thr Asp Gly Tyr Gln Ala Lys
            180                 185                 190
Gln Val Ile Pro Arg Asn Val Leu Asn Ser Ser Gln Tyr Tyr Tyr Ser
        195                 200                 205
Gly Asp Asp Leu Gly Asn Thr Tyr Thr Gln Lys Ala Thr Thr Phe Lys
210                 215                 220
Val Trp Ala Pro Thr Ser Thr Gln Val Asn Val Leu Leu Tyr Asp Ser
225                 230                 235                 240
Ala Thr Gly Ser Val Thr Lys Ile Val Pro Met Thr Ala Ser Gly His
                245                 250                 255
Gly Val Trp Glu Ala Thr Val Asn Gln Asn Leu Glu Asn Trp Tyr Tyr
        260                 265                 270
Met Tyr Glu Val Thr Gly Gln Gly Ser Thr Arg Thr Ala Val Asp Pro
        275                 280                 285
Tyr Ala Thr Ala Ile Ala Pro Asn Gly Thr Arg Gly Met Ile Val Asp
        290                 295                 300
Leu Ala Lys Thr Asp Pro Ala Gly Trp Asn Ser Asp Lys His Ile Thr
305                 310                 315                 320
Pro Lys Asn Ile Glu Asp Gly Val Ile Tyr Glu Met Asp Val Arg Asp
                325                 330                 335
Phe Ser Ile Asp Pro Asn Ser Gly Met Lys Asn Lys Gly Lys Tyr Leu
            340                 345                 350
Ala Leu Thr Glu Lys Gly Thr Lys Gly Pro Asp Asn Val Lys Thr Gly
        355                 360                 365
Ile Asp Ser Leu Lys Gln Leu Gly Ile Thr His Val Gln Leu Met Pro
    370                 375                 380
Val Phe Ala Ser Asn Ser Val Asp Glu Thr Asp Pro Thr Gln Asp Asn
385                 390                 395                 400
Trp Gly Tyr Asp Pro Arg Asn Tyr Asp Val Pro Glu Gly Gln Tyr Ala
                405                 410                 415
Thr Asn Ala Asn Gly Asn Ala Arg Ile Lys Glu Phe Lys Glu Met Val
            420                 425                 430
Leu Ser Leu His Arg Glu His Ile Gly Val Asn Met Asp Val Val Tyr
        435                 440                 445
Asn His Thr Phe Ala Thr Gln Ile Ser Asp Phe Asp Lys Ile Val Pro
    450                 455                 460
Glu Tyr Tyr Tyr Arg Thr Asp Asp Ala Gly Asn Tyr Thr Asn Gly Ser
465                 470                 475                 480
Gly Thr Gly Asn Glu Ile Ala Ala Glu Arg Pro Met Val Gln Lys Phe
                485                 490                 495
Ile Ile Asp Ser Leu Lys Tyr Trp Val Asn Glu Tyr His Ile Asp Gly
            500                 505                 510
Phe Arg Phe Asp Leu Met Ala Leu Leu Gly Lys Asp Thr Met Ser Lys
        515                 520                 525
```

```
Ala Ala Ser Glu Leu His Ala Ile Asn Pro Gly Ile Ala Leu Tyr Gly
        530                 535                 540

Glu Pro Trp Thr Gly Gly Thr Ser Ala Leu Pro Asp Asp Gln Leu Leu
545                 550                 555                 560

Thr Lys Gly Ala Gln Lys Gly Met Gly Val Ala Val Phe Asn Asp Asn
                565                 570                 575

Leu Arg Asn Ala Leu Asp Gly Asn Val Phe Asp Ser Ser Ala Gln Gly
            580                 585                 590

Phe Ala Thr Gly Ala Thr Gly Leu Thr Asp Ala Ile Lys Asn Gly Val
        595                 600                 605

Glu Gly Ser Ile Asn Asp Phe Thr Ser Ser Pro Gly Glu Thr Ile Asn
610                 615                 620

Tyr Val Thr Ser His Asp Asn Tyr Thr Leu Trp Asp Lys Ile Ala Leu
625                 630                 635                 640

Ser Asn Pro Asn Asp Ser Glu Ala Asp Arg Ile Lys Met Asp Glu Leu
                645                 650                 655

Ala Gln Ala Val Val Met Thr Ser Gln Gly Val Pro Phe Met Gln Gly
            660                 665                 670

Gly Glu Glu Met Leu Arg Thr Lys Gly Gly Asn Asp Asn Ser Tyr Asn
        675                 680                 685

Ala Gly Asp Ala Val Asn Glu Phe Asp Trp Ser Arg Lys Ala Gln Tyr
690                 695                 700

Pro Asp Val Phe Asn Tyr Tyr Ser Gly Leu Ile His Leu Arg Leu Asp
705                 710                 715                 720

His Pro Ala Phe Arg Met Thr Thr Ala Asn Glu Ile Asn Ser His Leu
                725                 730                 735

Gln Phe Leu Asn Ser Pro Glu Asn Thr Val Ala Tyr Glu Leu Thr Asp
            740                 745                 750

His Val Asn Lys Asp Lys Trp Gly Asn Ile Ile Val Val Tyr Asn Pro
        755                 760                 765

Asn Lys Thr Val Ala Thr Ile Asn Leu Pro Ser Gly Lys Trp Ala Ile
770                 775                 780

Asn Ala Thr Ser Gly Lys Val Gly Glu Ser Thr Leu Gly Gln Ala Glu
785                 790                 795                 800

Gly Ser Val Gln Val Pro Gly Ile Ser Met Met Ile Leu His Gln Glu
                805                 810                 815

Val Ser Pro Asp His Gly Lys Lys
            820

<210> SEQ ID NO 15
<211> LENGTH: 29
<212> TYPE: PRT
<213> ORGANISM: Artificial
<220> FEATURE:
<223> OTHER INFORMATION: synthetic modified pullulanase signal peptide

<400> SEQUENCE: 15

Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ser Ala
            20                  25

<210> SEQ ID NO 16
<211> LENGTH: 928
<212> TYPE: PRT
<213> ORGANISM: Artificial
<220> FEATURE:
<223> OTHER INFORMATION: synthetic modified pullulanase
```

<400> SEQUENCE: 16

```
Asp Gly Asn Thr Thr Thr Ile Ile Val His Tyr Phe Arg Pro Ala Gly
1               5                   10                  15
Asp Tyr Gln Pro Trp Ser Leu Trp Met Trp Pro Lys Asp Gly Gly Gly
            20                  25                  30
Ala Glu Tyr Asp Phe Asn Gln Pro Ala Asp Ser Leu Gly Ala Val Ala
        35                  40                  45
Ser Ala Asp Ile Pro Gly Asn Pro Ser Gln Val Gly Ile Ile Val Arg
    50                  55                  60
Thr Gln Asp Trp Thr Lys Asp Val Ser Ala Asp Arg Tyr Ile Asp Leu
65                  70                  75                  80
Ser Lys Gly Asn Glu Val Trp Leu Val Glu Gly Asn Ser Gln Ile Phe
                85                  90                  95
Tyr Ser Gln Lys Asp Ala Gln Asp Ala Ala Lys Pro Ala Val Ser Asn
            100                 105                 110
Ala Tyr Leu Asp Ala Ser Asn Gln Val Leu Val Lys Leu Ser Gln Pro
        115                 120                 125
Leu Thr Leu Gly Glu Gly Ala Ser Gly Phe Thr Val His Asp Asp Thr
130                 135                 140
Ala Asn Lys Asp Ile Pro Val Thr Ser Val Lys Asp Ala Ser Leu Gly
145                 150                 155                 160
Gln Asp Val Thr Ala Val Leu Ala Gly Thr Phe Gln His Ile Phe Gly
                165                 170                 175
Gly Ser Asp Trp Ala Pro Asp Asn His Ser Thr Leu Leu Lys Lys Val
            180                 185                 190
Thr Asn Asn Leu Tyr Gln Phe Ser Gly Asp Leu Pro Glu Gly Asn Tyr
        195                 200                 205
Gln Tyr Lys Val Ala Leu Asn Asp Ser Trp Asn Asn Pro Ser Tyr Pro
    210                 215                 220
Ser Asp Asn Ile Asn Leu Thr Val Pro Ala Gly Gly Ala His Val Thr
225                 230                 235                 240
Phe Ser Tyr Ile Pro Ser Thr His Ala Val Tyr Asp Thr Ile Asn Asn
                245                 250                 255
Pro Asn Ala Asp Leu Gln Val Glu Ser Gly Val Lys Thr Asp Leu Val
            260                 265                 270
Thr Val Thr Leu Gly Glu Asp Pro Asp Val Ser His Thr Leu Ser Ile
        275                 280                 285
Gln Thr Asp Gly Tyr Gln Ala Lys Gln Val Ile Pro Arg Asn Val Leu
    290                 295                 300
Asn Ser Ser Gln Tyr Tyr Tyr Ser Gly Asp Asp Leu Gly Asn Thr Tyr
305                 310                 315                 320
Thr Gln Lys Ala Thr Thr Phe Lys Val Trp Ala Pro Thr Ser Thr Gln
                325                 330                 335
Val Asn Val Leu Leu Tyr Asp Ser Ala Thr Gly Ser Val Thr Lys Ile
            340                 345                 350
Val Pro Met Thr Ala Ser Gly His Gly Val Trp Glu Ala Thr Val Asn
        355                 360                 365
Gln Asn Leu Glu Asn Trp Tyr Tyr Met Tyr Glu Val Thr Gly Gln Gly
    370                 375                 380
Ser Thr Arg Thr Ala Val Asp Pro Tyr Ala Thr Ala Ile Ala Pro Asn
385                 390                 395                 400
Gly Thr Arg Gly Met Ile Val Asp Leu Ala Lys Thr Asp Pro Ala Gly
                405                 410                 415
```

```
Trp Asn Ser Asp Lys His Ile Thr Pro Lys Asn Ile Glu Asp Glu Val
            420                 425                 430

Ile Tyr Glu Met Asp Val Arg Asp Phe Ser Ile Asp Pro Asn Ser Gly
            435                 440                 445

Met Lys Asn Lys Gly Lys Tyr Leu Ala Leu Thr Glu Lys Gly Thr Lys
        450                 455                 460

Gly Pro Asp Asn Val Lys Thr Gly Ile Asp Ser Leu Lys Gln Leu Gly
465                 470                 475                 480

Ile Thr His Val Gln Leu Met Pro Val Phe Ala Ser Asn Ser Val Asp
            485                 490                 495

Glu Thr Asp Pro Thr Gln Asp Asn Trp Gly Tyr Asp Pro Arg Asn Tyr
            500                 505                 510

Asp Val Pro Glu Gly Gln Tyr Ala Thr Asn Ala Asn Gly Asn Ala Arg
            515                 520                 525

Ile Lys Glu Phe Lys Glu Met Val Leu Ser Leu His Arg Glu His Ile
            530                 535                 540

Gly Val Asn Met Asp Val Val Tyr Asn His Thr Phe Ala Thr Gln Ile
545                 550                 555                 560

Ser Asp Phe Asp Lys Ile Val Pro Glu Tyr Tyr Arg Thr Asp Asp
            565                 570                 575

Ala Gly Asn Tyr Thr Asn Gly Ser Gly Thr Gly Asn Glu Ile Ala Ala
            580                 585                 590

Glu Arg Pro Met Val Gln Lys Phe Ile Ile Asp Ser Leu Lys Tyr Trp
            595                 600                 605

Val Asn Glu Tyr His Ile Asp Gly Phe Arg Phe Asp Leu Met Ala Leu
            610                 615                 620

Leu Gly Lys Asp Thr Met Ser Lys Ala Ala Ser Glu Leu His Ala Ile
625                 630                 635                 640

Asn Pro Gly Ile Ala Leu Tyr Gly Glu Pro Trp Thr Gly Gly Thr Ser
            645                 650                 655

Ala Leu Pro Asp Asp Gln Leu Leu Thr Lys Gly Ala Gln Lys Gly Met
            660                 665                 670

Gly Val Ala Val Phe Asn Asp Asn Leu Arg Asn Ala Leu Asp Gly Asn
            675                 680                 685

Val Phe Asp Ser Ser Ala Gln Gly Phe Ala Thr Gly Ala Thr Gly Leu
            690                 695                 700

Thr Asp Ala Ile Lys Asn Gly Val Glu Gly Ser Ile Asn Asp Phe Thr
705                 710                 715                 720

Ser Ser Pro Gly Glu Thr Ile Asn Tyr Val Thr Ser His Asp Asn Tyr
            725                 730                 735

Thr Leu Trp Asp Lys Ile Ala Leu Ser Asn Pro Asn Asp Ser Glu Ala
            740                 745                 750

Asp Arg Ile Lys Met Asp Glu Leu Ala Gln Ala Val Val Met Thr Ser
            755                 760                 765

Gln Gly Val Pro Phe Met Gln Gly Gly Glu Glu Met Leu Arg Thr Lys
            770                 775                 780

Gly Gly Asn Asp Asn Ser Tyr Asn Ala Gly Asp Ala Val Asn Glu Phe
785                 790                 795                 800

Asp Trp Ser Arg Lys Ala Gln Tyr Pro Asp Val Phe Asn Tyr Tyr Ser
            805                 810                 815

Gly Leu Ile His Leu Arg Leu Asp His Pro Ala Phe Arg Met Thr Thr
            820                 825                 830

Ala Asn Glu Ile Asn Ser His Leu Gln Phe Leu Asn Ser Pro Glu Asn
```

```
                835                 840                 845
Thr Val Ala Tyr Glu Leu Thr Asp His Val Asn Lys Asp Lys Trp Gly
        850                 855                 860

Asn Ile Ile Val Val Tyr Asn Pro Asn Lys Thr Val Ala Thr Ile Asn
865                 870                 875                 880

Leu Pro Ser Gly Lys Trp Ala Ile Asn Ala Thr Ser Gly Lys Val Gly
                885                 890                 895

Glu Ser Thr Leu Gly Gln Ala Glu Gly Ser Val Gln Val Pro Gly Ile
            900                 905                 910

Ser Met Met Ile Leu His Gln Glu Val Ser Pro Asp His Gly Lys Lys
        915                 920                 925

<210> SEQ ID NO 17
<211> LENGTH: 4
<212> TYPE: PRT
<213> ORGANISM: Artificial
<220> FEATURE:
<223> OTHER INFORMATION: synthetic peptidase target consensus sequence

<400> SEQUENCE: 17

Ala Ser Ala Ala
1
```